(12) United States Patent
Bradley et al.

(10) Patent No.: US 6,395,487 B1
(45) Date of Patent: May 28, 2002

(54) METHOD CHROMOSOMAL REARRANGEMENT BY CONSECUTIVE GENE TARGETING OF TWO RECOMBINATION SUBSTRATES TO THE DELETION ENDPOINTS

(75) Inventors: Allan Bradley, Houston; Ramiro Ramirez-Solis, Missouri City, both of TX (US); Pentao Liu, Frederick, MD (US); Hong Su; Binhai Zheng, both of Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/552,219

(22) Filed: Apr. 19, 2000

Related U.S. Application Data

(63) Continuation of application No. 08/883,616, filed on Jun. 26, 1997, now Pat. No. 6,077,667
(60) Provisional application No. 60/020,620, filed on Jun. 26, 1996.

(51) Int. Cl.$^7$ ............................ C12Q 1/68; C12N 1/63; C12N 15/87; C07H 21/04
(52) U.S. Cl. ........................ 435/6; 435/320.1; 435/462; 536/23.1
(58) Field of Search ........................ 435/6, 320.1, 462; 536/23.1

(56) References Cited

U.S. PATENT DOCUMENTS 5,679,523 A    10/1997   Li et al.

OTHER PUBLICATIONS

Ramirez–Solis et al. Chromosome engineering in mice. Nature vol. 378:720–724. Dec. 14, 1995.*
Zhi–Wei Li et al., Proc. Natl. Acad. Sci. USA vol. 93, p. 6158–6162 (1996).
M. Nehls et al., BioTechniques vol. 17, p. 770–775 (1994).
Bernadette Holdener–Kenny et al., BioEssays vol. 14 No. 12, p. 831–839 (1992).
Andrew Smith et al., Nature Genetics vol. 9, p. 376–385 (1995).
Hua Gu et al., Science vol. 265, p. 103–106 (1994).
Brian Sauer et al., Nucl. Acids Res. vol. 17, p. 147–161 (1989).
Peter Fuller et al., Molec. Endocrinol vol. 1 No. 4, p. 306–311 (1987).
Van Luu The et al., Mole. Endocrinol vol. 3 No. 8, p. 1301–1309 (1989).
Henk Roelink et al. PNAS USA vol. 87, p. 4519–4523 (1990).
Hua Gu et al., Cell vol. 73, p. 1155–1164 (1993).
Melissa Rubock et al., PNAS USA vol. 87, p. 4751–4755 (1990).
Yoshio Miki et al., Science vol. 266, p. 66–71 (1994).

* cited by examiner

Primary Examiner—Terry McKelvey
Assistant Examiner—William Sandals
(74) Attorney, Agent, or Firm—Fulbright & Jaworski

(57) ABSTRACT

The present invention involves the creation of defined chromosomal deficiencies, inversions and duplications using Cre recombinase in ES cells transmitted into the mouse germ line. These chromosomal reconstructions can extend up to 3–4 cM. Chromosomal rearrangements are the major cause of inherited human disease and fetal loss. Additionally, translocations and deletions are recognized as major genetic changes that are causally involved in neoplasia. Chromosomal variants such as deletions and inversions are exploited commonly as genetic tools in organisms such as Drosophila. Mice with defined regions of segmental haploidy are useful for genetic screening and allow accurate models of human chromosomal diseases to be generated.

19 Claims, 20 Drawing Sheets

| Orientation | Phase | HAT$^R$ products |
|---|---|---|
| AA | cis | del |
| | trans | del + dup |
| BA | cis | inv |
| | trans | dicen + ditel |
| AB | cis | inv |
| | trans | dicen + ditel |
| BB | cis | dup |
| | trans | dup + del |

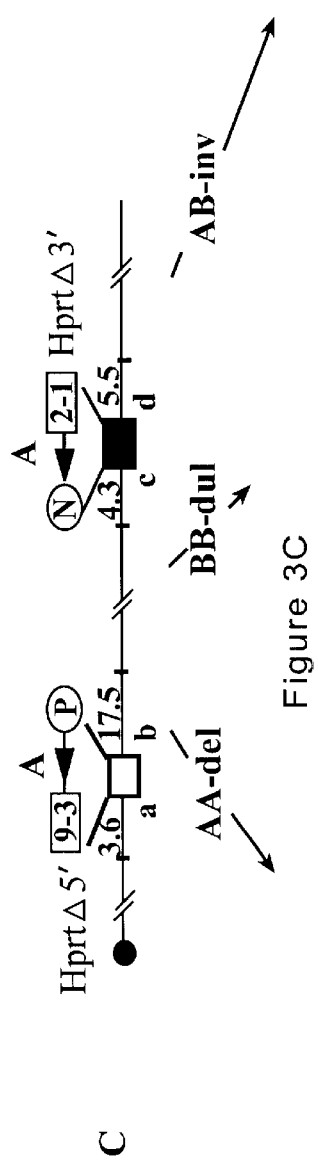
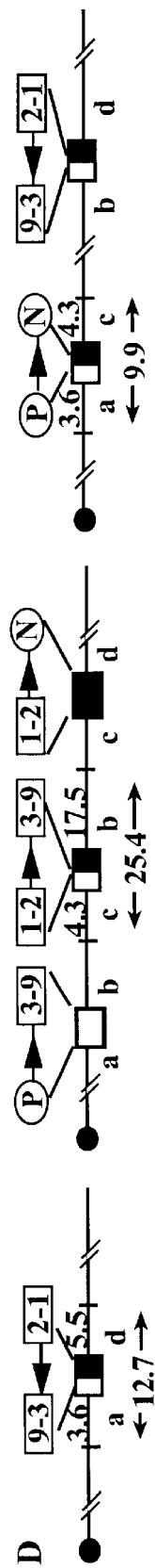
Figure 3C
Figure 3D

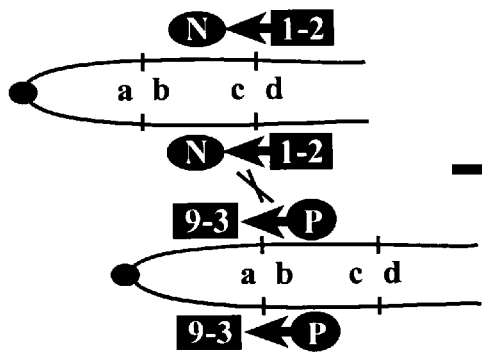
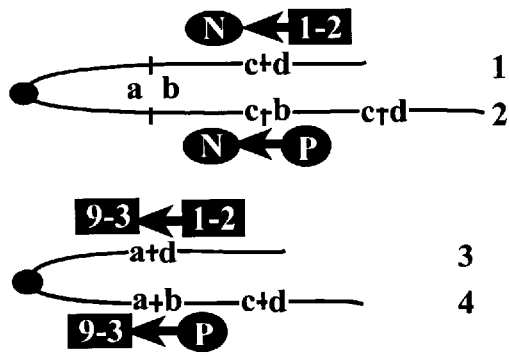
Figure 4A
Figure 4B
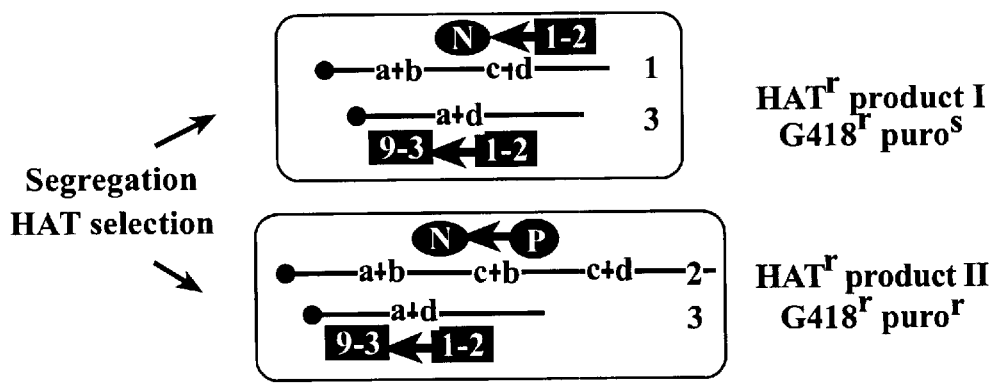
Figure 4C

Mouse Chromosome 11

*Cis*: deletion

*Trans*: deletion and duplication

METHOD CHROMOSOMAL REARRANGEMENT BY CONSECUTIVE GENE TARGETING OF TWO RECOMBINATION SUBSTRATES TO THE DELETION ENDPOINTS

This is a continuation of application Ser. No. 08/883,616 filed on Jun. 26, 1997 now U.S. Pat. No. 6,077,667, which claims priority to the U.S. provisional application Ser. No. 60/020,620, filed on Jun. 26, 1996.

The present invention was made utilizing funds of the United States Government. The U.S. Government is entitled to certain rights under this invention.

BACKGROUND OF THE INVENTION

1. Technical Field of the Invention

The present invention involves the creation of defined chromosomal deficiencies, inversions and duplications using Cre recombinase in embryonic stem cells and transmitted into the mouse germ line. In the present invention, these chromosomal reconstructions can extend up to 3–4 cM. Chromosomal rearrangements are the major cause of inherited human disease and fetal loss. Further, chromosomal translocations and deletions are recognized as major genetic changes that are causally involved in neoplasia. Chromosomal variants such as deletions and inversions are exploited commonly as genetic tools in diploid organisms such as Drosophila. In diploid organisms, such deficiencies are exploited in genetic screens because a small portion of the genome is functionally hemizygous. Thus, a mutation which would normally be recessive and masked by the wildtype allele in a diploid context will be dominant and detectable in the haploid state. In the mouse, deficiencies have not, up to now, been available generally; thus, screens for recessive mutations are nonexistent or particularly cumbersome. However, the present invention provides methods to engineer mice and cell lines with defined regions of segmental haploidy. Such mice are useful for genetic screening and provide accurate models of human chromosomal diseases.

2. The Prior Art

Inherited chromosomal rearrangements such as inversions, duplications and deficiencies are responsible for a significant fraction of human congenital disease. Chromosomal changes also occur somatically and are associated with neoplastic disease. Defining the causal genetic alteration in a region of the genome associated with chromosomal rearrangements can be relatively straightforward if the affected gene lies in the breakpoint of an inversion or translocation. However, in cases of duplications and deficiencies, the specific genetic lesion(s) associated with pathological chromosomal changes are much harder to identify. Still, the generation of animal models that accurately recapitulate the genetic lesion would facilitate the study of disease and could be very helpful in the efforts to dissect specific gene-function relationships in multigene syndromes.

In diploid organisms such as Drosophila, chromosomal deficiencies are commonly exploited in genetic screens because a small portion of the genome is functionally hemizygous. Thus, a mutation which would be recessive and masked by the wildtype allele in the diploid context will be dominant and therefore readily detectable in the haploid state. In the mouse, deficiencies are not available generally. Despite the limited number of deficiencies available in the mouse, the potential for the detailed analysis of a genetic interval using these deficiencies has been demonstrated clearly. See Holdener-Kenny, et al., *BioEssays*, 14:831–39 (1992), which is hereby incorporated by reference.

Deficiencies that are available currently in the mouse genome were generated at random using ionizing irradiation. Although conventional gene targeting technology in embryonic stem (ES) cells can generate virtually any type of mutation, including deletions of up to 20 kb, it has not been possible to delete substantially larger fragments by using standard methodology. Likewise, the technology required to construct large inversions and duplications has not been established.

One mechanism by which chromosomes may be engineered is by the use of Cre recombinase. Cre recombinase has been used in mammalian cell lines and in vivo to delete or invert sequences between the 34 base pair recognition sequences, loxP sites, placed a few kb apart on the same chromosome. The recombination is initiated by Cre proteins which bind to 13-bp inverted regions in the loxP sites and promote synapses or joining of a pair of sites. Next, the Cre proteins catalyze strand exchange between the pair of sites within an asymmetric 8-bp central spacer sequence by concerted cleavage and rejoining reactions, involving a transient DNA-protein covalent linkage. Smith, et al., *Nature Genetics*, 9:376–385 (1995); Gu, et al., *Science*, 265:103–06 (1994) and Sauer, *Nucl. Acids Res.*, 17:147–61 (1989) (both of these references are hereby incorporated by reference). Additionally, recombinases have been used to induce mitotic recombination between homologous and non-homologous chromosomes in Drosophila, plants and mammalian cells. Embryonic stem cell technology has become a powerful tool for defining the function of mammalian genes, but mainly has been restricted to the mutation of single genes. Replacement vectors have been used to construct deletions of up to 19 kb; however, utilizing the same strategy to construct larger deletions (>60 kb) has not been successful. In the present invention, the generation and direct selection of deletions, duplications and inversions, ranging from 90 kb to 3–4 cM, in ES cells is demonstrated.

SUMMARY OF THE INVENTION

The method of the present invention is based on consecutive gene targeting of two recombination substrates to the deletion endpoints and the subsequent induction of recombination mediated by the Cre recombinase. This method generates a positive selectable marker allowing for the direct selection of clones with the desired chromosome structures. Despite the multitude of steps involved in generating these rearrangements in ES cells, deletion and duplication alleles have been transmitted into the mouse genome.

One object of the present invention is a method for causing a large-scale chromosomal rearrangement by first deleting a portion of genetic material.

An additional object of the present invention is a targeting vector system capable of inserting into two endpoint regions constraining a desired chromosomal deletion.

Thus in accomplishing the foregoing objects, there is provided in accordance with one aspect of the present invention a method for deleting a selected region of genetic material in cells comprising the steps of: inserting a first selection cassette at a 5' end of said selected region using conventional gene targeting methods, said first selection cassette comprising a first selectable marker, a first loxP recombination site, and a first portion of a second selectable marker; selecting cells expressing said first selectable marker; inserting a second selection cassette at a 3' end of said selected region using conventional gene targeting methods, said second selection cassette comprising a third selectable marker, a second loxP recombination site, and a remaining portion of said second selectable marker; selecting cells expressing said third selectable marker; expressing Cre recombinase to produce recombination between said first and second loxP sites; and selecting cells expressing said second selectable marker.

Specific embodiments of the above method can include a puromycin resistance gene as the first selectable marker, a functional Hprt gene as the second selectable marker, and a neomycin resistance gene as the third selectable marker. Numerous other selectable markers will work, their presence in the particular deletion strategy is merely to aid cell selection. In other preferred embodiments, the first selectable marker is a puromycin resistance gene. In still other preferred embodiments, the second selectable marker is a functional Hprt gene. And in still other preferred embodiments, the third selectable marker is a neomycin resistance gene.

In still other preferred embodiments, the cells referred to above are embryonic stem cells, though significant, they need not be stem cells. In other preferred embodiments, the cells are embryonic stem cells, and said cells develop into mice. And in yet other preferred embodiments, the cells are embryonic stem cells, and said cells are maintained as cell lines.

In yet another preferred embodiment, a viral vector is used to replace either or both native sequences of DNA. In one embodiment, this virus is a retrovirus. In yet another embodiment, the viral vector referred to above has a provirus structure comprising a cassette in turn comprising: an hprtΔ5' cassette, a loxP site, and a puromycin resistance gene.

In yet another particularly preferred embodiment, the method for deleting a portion of chromosomal material in cells wherein the targeting vectors are a first targeting vector for replacing said first native sequence of DNA at said 5' end, comprising: a genomic insert cloned into the vector of about 7.5 kb; a tyrosinase minigene; a Neo$^r$ gene; a 5' hprt fragment; and a loxP site embedded into said hprt fragment; and a second targeting vector for replacing said second native sequence of DNA at said 3' end, comprising: a genomic insert cloned into the vector of about 8.5 kb; a K14Agouti gene; a Puro$^r$ gene; a 3' hprt fragment; and a loxP site embedded into said hprt fragment.

In one particularly preferred embodiment of the second aspect of the present invention, there is provided a replacement vector system comprising a first targeting vector for replacing said first native sequence of DNA at said 5' end, comprising a genomic insert cloned into the vector of about 7.5 kb; a tyrosinase minigene; a Neo$^r$ gene; a 5' hprt fragment; and a loxP site embedded into said hprt fragment; and a second targeting vector for replacing said second native sequence of DNA at said 3' end, comprising: a genomic insert cloned into the vector of about 8.5 kb; a K14Agouti gene; a Puro$^r$ gene; a 3' hprt fragment; and a loxP site embedded into said hprt fragment.

BRIEF DESCRIPTION OF THE FIGURES

FIGS. 4A–4C: $G_2$ trans recombination between homologous chromosomes. 4A: depicts individual sister chromatids from chromosome homologues still joined at the centromere. One chromosome is illustrated with hprt$_A$5, the neomycin resistance gene (N) used for targeting. The other homologue was targeted with hprt$_A$3 cassette linked to the puromycin resistance gene (P). Cre-induced recombination between loxP sites on sister chromatids from different homologues is illustrated by an X. B: illustrates the recombinant structure of the sister chromatids. The individual chromatids are numbered 1–4. Chromatid 3 carries the reconstructed Hprt minigene and the deletion. 4C: shows the results of HAT selection for chromatid 3 which will segregate with either chromatid 1 or 2 which carries only the neo or both the neo and puro cassettes, respectively. The chromatid 2+3 segregant carries a duplication and deletion (genetically balanced) and is indistinguishable from the $G_1$ interchromosomal product. The chromatid 1+3 product carries the deletion and the original single targeted chromosome; this can only have arisen via the $G_2$ pathway.

DETAILED DESCRIPTION OF THE INVENTION

Figure 1A:
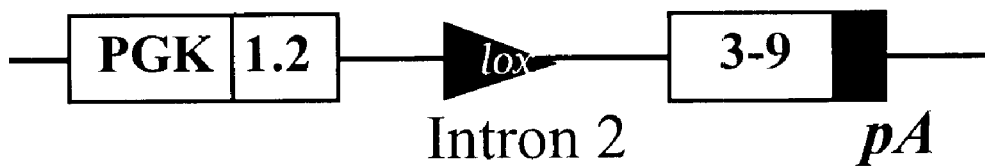
FIGS. 1A–1E: 1A: depicts the Hprt-loxP minigene cassette; 1B: depicts the hprt$_A$5 and hprt$_A$3 recombination substrates; 1C: outlines the general strategy for Cre-induced, targeted genomic rearrangements illustrated at the HoxB cluster—only the intrachromosomal pathway is shown; 1D: demonstrates alternative orientations (A or B) of the recombination substrates at the E2DH and Gastrin loci; 1E: shows chromosomal alterations induced by Cre recombinase for the different orientations of the minigenes in cis and trans.
Figure 1B:
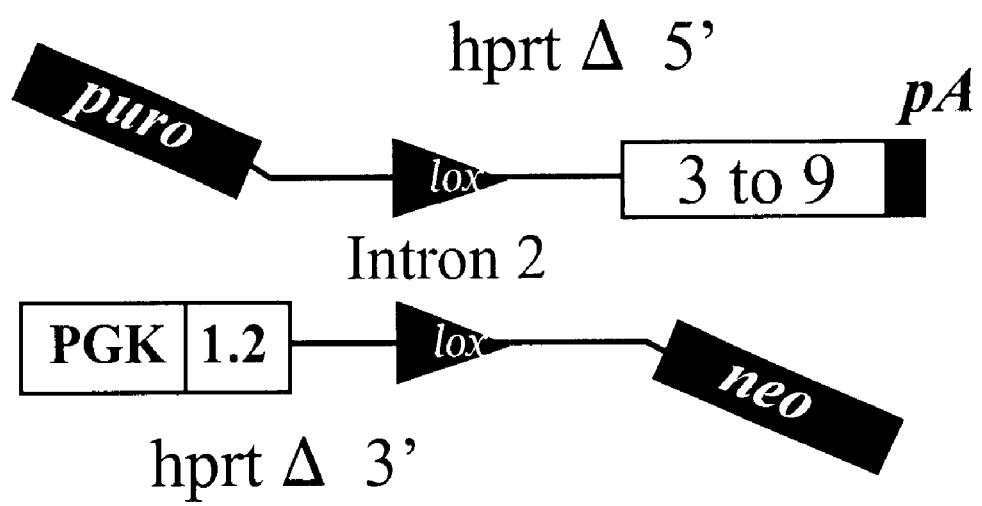

It will be apparent readily to one skilled in the art that various substitutions and modifications may be made to the invention disclosed herein without departing from the scope and spirit of the invention.

As used herein, the term "chromosome engineering" means creating chromosome inversions, duplications or deletions.

As used herein, the term "chromosome deficiency" means a lack of a chromosome or portion of a chromosome.

As used herein, the term "chromosome inversion" means reversal of a part of a chromosome so that the genes within that part are in reverse order.

As used herein, the term "chromosome duplication" means an extra, duplicate chromosome or part of a chromosome.

As used herein, the term "ES cell" stands for embryonic stem cells: cells which are derived from early mouse embryos that can be maintained in an undifferentiated state, but, upon return to the environment of the early embryo, can contribute to all types of cells in the resulting chimera.

As used herein, the term "Cre-induced recombination" means catalysis of both intramolecular and intermolecular recombination by the Cre protein. The Cre protein is a 38 kD protein that recombines DNA between specific, 34 bp sequences called loxP sites.

As used herein, the term "interchromosomal recombination" means recombination between different chromosomes.

As used herein, the term "intrachromosomal recombination" means recombination between regions on the same chromosome.

As used herein, the term "HoxB" refers to a specific gene cluster having the same physical distance as a P1 phage and having known structure and orientation.

As used herein, the term "Hoxb-9" refers to a specific gene in the HoxB gene cluster.

As used herein, the term "Hoxb-1" means the 3'-most gene of the HoxB gene cluster.

As used herein, the term "hprt" means hypoxanthine phosphoribosyltransferase.

As used herein, the term "loxP site" means the specific 34 bp sequence recognized by Cre recombinase.

As used herein, the term "G418 resistance" means having a gene which confers resistance to G418.

As used herein, the term "neo resistance" means having a gene which confers resistance to G418.

As used herein, the term "puromycin resistance" means having a gene which confers resistance to puromycin.

As used herein, the term "HAT resistance" means cells resistant to media containing hypoxanthine, aminopterin and thymine. Only cells expressing the Hypoxanthine phosphoribosyl transferase (Hprt) and thymidine kinase genes will grow in HAT medium.

As used herein, the term "targeting deletion" means a planned deletion created by targeting an area for recombination by insertion of a loxP or other recombination site.

As used herein, the term "germ line transmission" refers to a chimeric animal capable of transmitting a particular trait to its offspring.

As used herein, the term "hemizygous" means genes present only once in a genotype.

As used herein, the term "heterozygous" refers to the state of an organism having two different alleles at a given locus on homologous chromosomes.

As used herein, the term "homozygous" refers to the state of an organism having the same two alleles at a given locus on homologous chromosomes.

As used herein, the term "Gastrin" locus means a gene on mouse chromosome 11 which encodes a peptide involved in stimulating acid secretion in the stomach. See Fuller et al., *Molec Endocrinol.* 1:306–11 (1987).

As used herein, the term "E2DH" locus, also known as 17HSD, is a gene whose product is involved in steroid biosynthesis. This dehydrogenase converts estrone to estradiol. See The et al., *Molec. Endocrinol.* 3:1301–06 (1989).

As used herein, the term "Wnt3" locus is a gene which encodes a member of the wnt family of growth factors. Wnt3 is a target for activation by MMTV which causes mammary tumors. Roelink et al., PNAS 87:4519 (1990).

As used herein, the term "selected region" refers to that particular region of the chromosome targeted for manipulation (i.e., deletion, inversion, duplication).

In one embodiment of the present invention, a method is disclosed and claimed for deleting a selected region of genetic material in cells comprising the steps of: inserting a first selection cassette at a 5' end of said selected region using conventional gene targeting methods, said first selection cassette comprising a first selectable marker, a first loxP recombination site, and a first portion of a second selectable marker; selecting cells -expressing said first selectable marker; inserting a second selection cassette at a 3' end of said selected region using conventional gene targeting methods, said second selection cassette comprising a third selectable marker, a second loxP recombination site, and a remaining portion of said second selectable marker; selecting cells expressing said third selectable marker; expressing Cre recombinase to produce recombination between said first and second loxP sites; and selecting cells expressing said second selectable marker.

In particularly preferred embodiments of the present invention, the method referred to above uses a first selectable marker, a puromycin resistance gene, said second selectable marker is an Hprt gene, and said third selectable marker is a neomycin resistance gene.

In another particularly preferred embodiment, the first selectable marker is a puromycin resistance gene. In yet another particularly preferred embodiment, the second selectable marker is a functional Hprt gene. In still another preferred embodiment, the third selectable marker is a neomycin resistance gene. In another preferred embodiment, the cells are embryonic stem cells. In still another preferred embodiment, the cells are embryonic stem cells, and said cells develop into mice. In still another preferred embodiment, the cells are embryonic stem cells, and said cells are maintained as cell lines. In another embodiment of the present invention, Cre is transiently expressed Cre. In other embodiments, it is expressed either inducibly or constitutively.

In a second general embodiment of the present invention, a method is disclosed and claimed for deleting a selected region of genetic material in cells comprising the steps of: inserting a first selection cassette at a 5' end of said selected region using either conventional targeting methods or a viral vector, said first selection cassette comprising a first selectable marker, a first loxP recombination site, and a first portion of a second selectable marker; selecting cells expressing said first selectable marker; inserting a second selection cassette at a 3' end of said selected region using conventional gene targeting methods or a viral vector, said second selection cassette comprising a third selectable marker, a second loxP recombination site, and a remaining portion of said second selectable marker; selecting cells expressing said third selectable marker; expressing transiently Cre recombinase to produce recombination between said first and second loxP sites; and selecting cells expressing said second selectable marker.

In one particularly preferred embodiment, the viral vector is a retrovirus. In yet another particularly preferred embodiment, the viral vector has a provirus structure comprising a cassette in turn comprising an hprtΔ5' cassette, a loxp site, and a puromycin resistance gene. In yet another particularly preferred embodiment, the viral vector has a provirus structure comprising a cassette in turn comprising an hprtΔ5' cassette, a loxp site, and a neomycin resistance gene. In still another particularly preferred embodiment, the targeting or viral vectors are a first vector for inserting said first native sequence of DNA at said 5' end, comprising: a genomic insert cloned into the vector of about 7.5 kb; a tyrosinase minigene; a Neo$^r$ gene; a 5' hprt fragment; and a loxp site embedded into said hprt fragment; and a second vector for inserting said second native sequence of DNA at said 3' end, comprising: a genomic insert cloned into the vector of about 8.5 kb; a K14-Agouti gene; a purorgene; a 3' hprt fragment; and a loxp site em bedded into said hprt fragment.

In a third general embodiment of the present invention, a replacement vector system, is disclosed and claimed comprising: a first vector for inserting said first native sequence of DNA at said 5' end, comprising: a genomic insert cloned into the vector of about 7.5 kb; a tyrosinase minigene; a Neo$^r$ gene; a 5' hprt fragment; and a loxP site embedded into said hprt fragment; and a second vector for inserting said second native sequence of DNA at said 3' end, comprising: a genomic insert cloned into the vector of about 8.5 kb; a K14-Agouti gene; a Puro$^r$ gene; a 3' hprt fragment; and a loxP site embedded into said hprt fragment.

In a fourth general embodiment of the present invention, there is disclosed and claimed a method for creating defined chromosomal deficiencies, deletions, and duplications comprising the steps of: identifying a desired region of a chromosome of interest to be deleted; inserting two native sequences at each endpoint of said region of said chromosome of interest using a first and a second targeting vector, each comprised of one or more selectable markers and a loxP site and an hprt fragment; transiently expressing Cre recombinase to produce recombination between each of two said loxP sites; whereby upon chromosomal rearrangement induced by said Cre recombinase, a functional Hprt expression cassette is reconstructed.

Other and further embodiments, features and advantages will be apparent and the invention more readily understood from a reading of the following Examples and by reference to the accompanying drawings forming a part thereof, wherein the examples of the presently preferred embodiments of the invention are given for the purposes of disclosure.

EXAMPLE A

General Strategies

The various chromosomal rearrangements described herein are designed with strong positive selection for the desired chromosomal change. Very generally, this was accomplished by targeting consecutively complementary, overlapping but non-functional hprt-loxP expression cassettes to the endpoints of a chromosomal interval. Cre expression (either transiently, inducibly, or constitutively) in these double-targeted ES cells induces loxP recombination resulting in chromosomal rearrangements specific to the relative orientation of the loxP sites. Since the loxP sites are imbedded in the hprt minigene fragments, the chromosomal rearrangement will also reconstruct a functional hprt expression cassette, therefore facilitating direct positive selection for the clones with these alterations.

The use of mouse ES (embryonic stem) cells is preferable, though not required, to execute the method the present invention. Use of these cells would, of course, allow large-scale chromosome manipulation to be introduced into a germ line, which would in turn facilitate enhanced functional study of the mouse genome.

The loxP sites were introduced by conventional gene targeting protocols or by viral vectors into the endpoints of the region which was to be rearranged. Or, one endpoint can be introduced by conventional methods, and the other introduced by a viral vector. To maximize the ability to select for the rare ES cell clones in which Cre expression had successfully induced recombination between loxP sites, the individual loxP sites targeted to the endpoints of the chromosomal rearrangement were imbedded in two complementary but non-functional fragments of an Hprt minigene cassette. Recombination between the loxP sites would restore the activity of this cassette, facilitating the direct selection in HAT media of only those recombinant ES cells with the desired chromosomal structure (FIGS. 1A and B).

In one particularly preferred embodiment of the present invention, the complementary recombination/selection substrates consist of overlapping, but incomplete, pieces of an Hprt minigene with a loxP site in the intron. These minigene fragments are linked to different positive selection cassettes which are required for selection during gene targeting. The 5' fragment of the loxP-Hprt minigene is linked to a neomycin resistance gene ($hprt_A3'$ cassette), while the 3' fragment is linked to a puromycin resistance gene ($hprt_A5'$ cassette). Cre-induced recombination between the loxP sites generates a fully-functional Hprt minigene which provides resistance to HAT selection in Hprt-deficient cells. The positive selectable markers are positioned so that following recombination, they are lost from the deleted chromosome. All of the clones that survive selection have the desired chromosomal structure. A similar positive selection system for detecting a chromosomal translocation has recently been reported by Smith et al., *Nature Genetics* 9:376–385 (1995). In addition, genes such as K14-agouti and tyrosinase genes can be preferably inserted into the vectors for use as color-coat markers, to aid in selecting the members of the population for which the chromosomal insert was successful. Albino mice lack the tyrosinase gene, so reinsertion of that gene is manifest by black mice in a population of white mice. Similarly, the k14-agouti gene gives yellow color to the tips of the coat hairs against a black background (i.e., it makes black mice appear brown).

Initially, a small deletion (90 kb) was constructed which encompasses the HoxB locus since the gene order and orientation was known. Subsequently, much larger chromosomal alterations were generated. For the latter alterations, knowledge of the transcriptional direction of the genes which serve as the rearrangement endpoints was not available. Consequently, it was necessary to generate ES cell lines with the four possible configurations of the hprt minigene fragments. Because the transcriptional direction of the genes relative to the centromere was also unknown, it was not possible to predict which combination of orientations would give a deletion; however, clones with deletions are readily distinguished in culture from the clones with other classes of recombinant chromosomes because in addition to becoming HAT resistant, both of the positive selection markers are lost. The generation of a deletion reveals the relative transcriptional direction of the two deletion endpoints, and if the proximal-distal map positions are known (which was the case in these experiments), further deletions from the same endpoint are greatly simplified.

The frequency of recombination between the loxP sites when they were on the same chromosome varied from $6 \times 10^{-7}$ to $5 \times 10^{-5}$, but a direct relationship between the distance and the frequency was not apparent. The frequency of recombination was, however, significantly lower than those reported when the loxP sites are a few kb apart; see, Gu, et al., Cell 73:1155–64 (1993), verifying that selection is required to isolate these clones. These frequencies are derived by the transient transfection of Cre in ES cells, but might be higher under conditions of constitutive expression of Cre, for example, in a specific lineage in a transgenic mouse. The frequency of recombination was reduced by one to two orders of magnitude when the loxP sites were integrated in trans compared to the cis configuration. This is consistent with the knowledge that individual chromosomes occupy discrete, non-overlapping domains in an interphase nucleus.

HAT-resistant clones derived from the trans configuration of the double-targeted clones oriented to give deletion products were not expected to become G418 or puro sensitive. But approximately half of the HAT-resistant clones segregated the puro cassette while all retained the neo cassette. This segregation pattern is consistent with inter-sister-chromatid recombination (see FIG. 4). Although the number of clones with the trans configuration was relatively small, the equal ratio of puro+neo to neo-only segregants suggests that $G_2$ recombination is the predominant pathway used in this case. The rescue of hprt negative daughter cells by metabolic cooperation also suggests that a substantial fraction of the HAT-resistant clones derived from the cis double-targeted clones may have been generated by the sister-chromatid pathway.

The correlation of the induced chromosomal rearrangements with the orientation of the vectors has revealed physical mapping information in this region of mouse chromosome 11. For instance, the genes described in the following Examples, Gastrin, E2DH, Wnt 3 and the Hox B cluster, are all transcribed in the centromere-to-telomere direction. The E2DH-HoxB deletion has shown that the HoxB cluster is oriented with the Hoxb-9 gene nearest to the centromere.

EXAMPLE B

Deletion and Duplication of 90 kb Containing the HoxB Cluster

The HoxB cluster provides an excellent substrate for the deletion strategy since the cluster is about the same physical distance as a P1 phage and the structure and orientation of the individual genes is known. See, Rubock, et al., *PNAS USA* 87:4751–55 (1990). Moreover, a deletion allele of HoxB is very useful for detailed genetic analysis of this region.

Figure 1C:
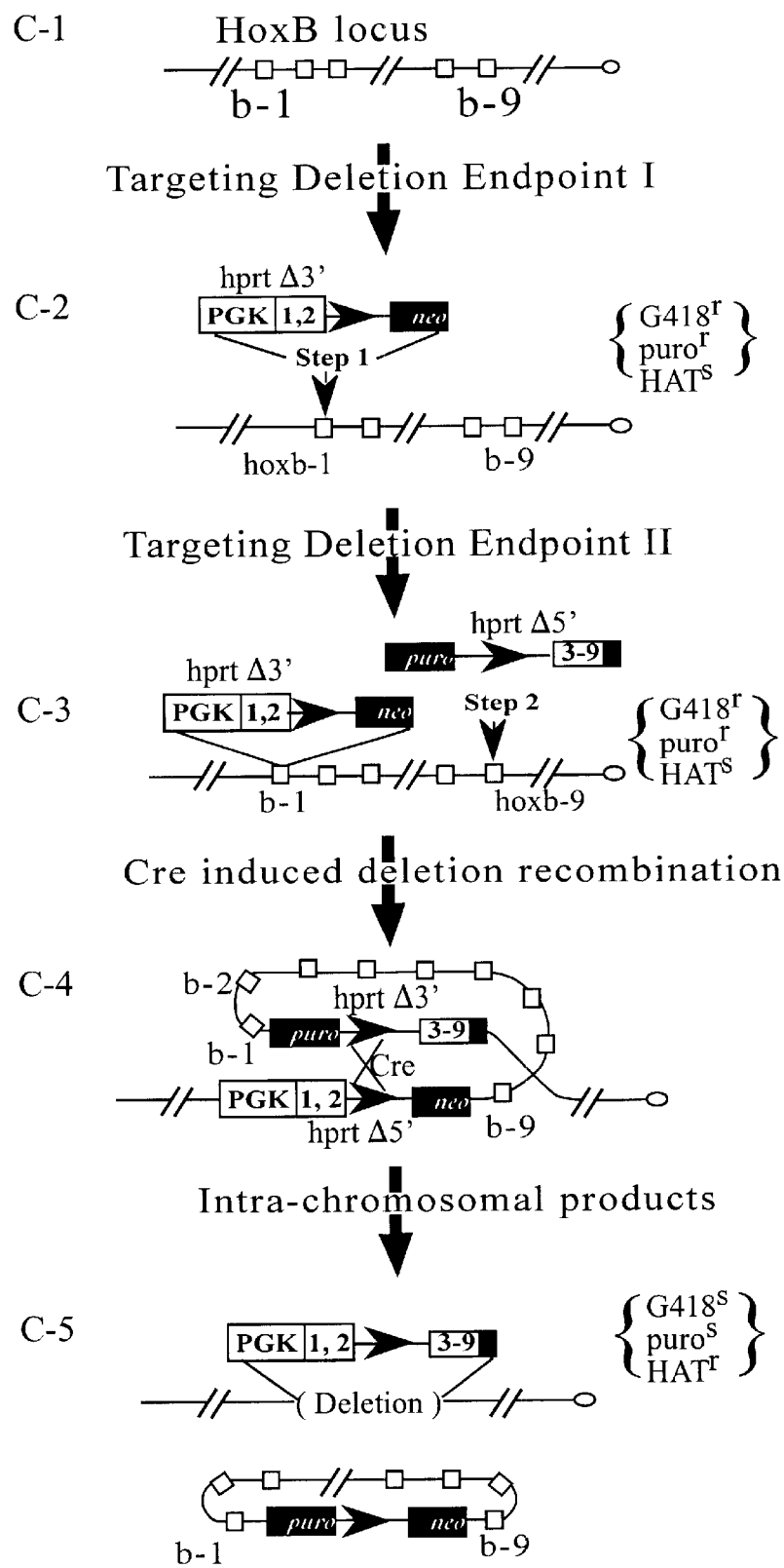
Figures 1D, 1E:
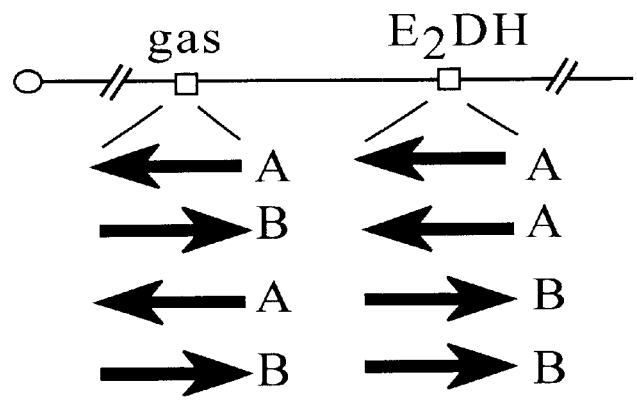
Figure 2A:
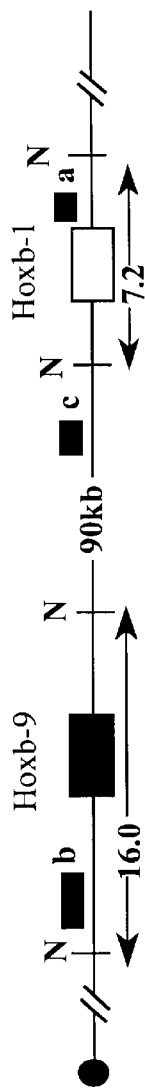
FIGS. 2A–2F: Shows the results of a Southern blot analysis of the chromosomal engineering technology used to delete the HoxB cluster. A–C demonstrates the interpretation of, and D–F shows the actual Southern blot data from wildtype (wt), double targeted (dt) or HAT resistant ES cell clones (lanes 1 and 2). M1 and M2 are HindIII-cut and BstEII-cut lambda DNA molecular weight markers, respectively. Hoxb-1 is located in a 7.2 kb NheI fragment detected with probe a (2A and 2D; this allele is present in all of the lanes). Targeting of the hprt$_A$3 -neo cassette to the Hoxb-1 locus generates a novel 10.2 kb NheI restriction fragment detected with probe a (2B and 2D dt). Hoxb-9 is located on a 16 kb NheI restriction fragment detected with probe b (2A and 2E; this allele is present in all of the lanes). Targeting of the hprt$_A$5 -puro to the Hoxb-9 gene generates a novel 20.4 kb NheI restriction fragment detected with probe b (2B and 2E dt). Cre-induced recombination brings together the hprt$_A$5 and hprt$_A$3 and produces a NheI 18.2 kb deletion-specific junction fragment detected by both probes a and b (2C, 2D 1 and 2). Probe c, located in the deletion region, shows a dosage difference in Panel 2F, 1 and 2, compared to the wt and dt lanes. Probe a is a 0.7 kb RsaI fragment located approximately 3 kb downstream of Hoxb-1 exon 2; probe b is a 1 kb RsaI fragment located approximately 5 kb upstream of Hoxb-1 exon 1. P and N represent the puromycin and neomycin selection cassettes.
Figure 2B:
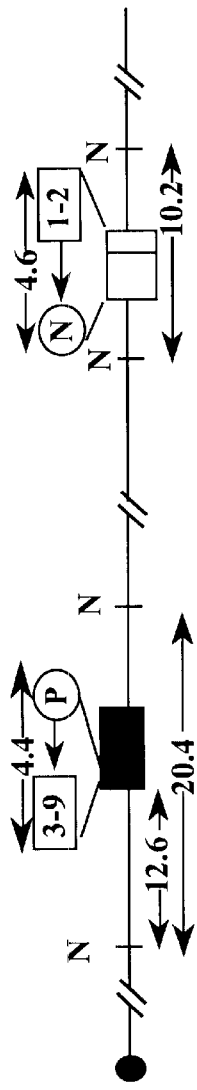
Figure 2C:
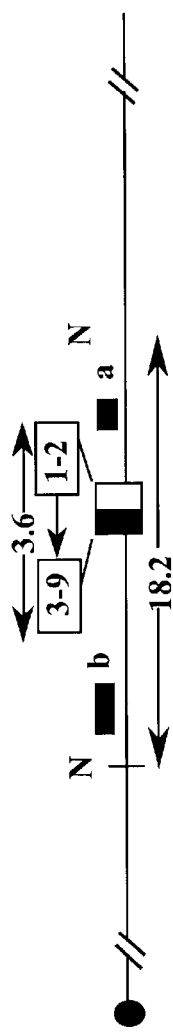
Figure 2D:
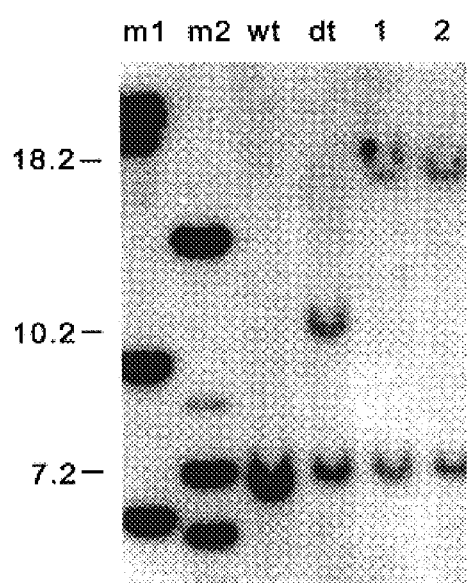
Figure 2E:
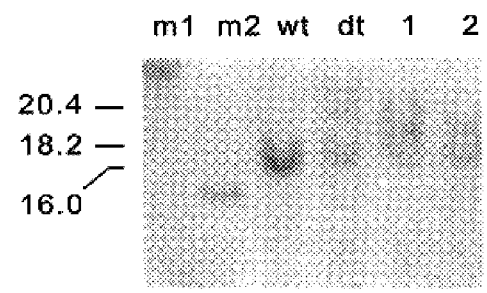
Figure 2F:
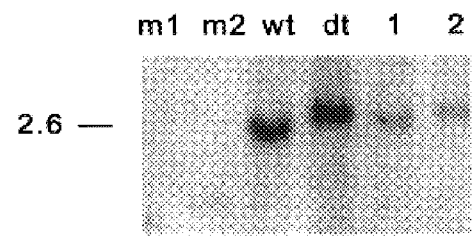

To generate a HoxB deletion allele, the strategy outlined in FIG. 1 was followed. The $hprt_A3'$ cassette was used to construct a targeting vector for Hoxb-1, the most 3' gene of the cluster, and targeted clones were identified (FIG. 2). An ES clone with the Hoxb-1 targeted allele (FIG. 2B) was expanded and transfected with the Hoxb-9 targeting vector containing the complementary $hprt_A5'$ cassette. The minigene fragments were oriented in the targeting vectors so that, after targeting, they would be in the correct order and orientation with the positive selection cassettes (neo and puro) located between the loxP sites (FIG. 2C). Double-targeted clones were identified (FIG. 2C), and half of these clones would be expected to have both targeted alleles on the same chromosome (cis) and half should have the targeted alleles on different homologues (trans).

To induce the recombination between the loxP sites, several independent double-targeted (Hoxb-1 and Hoxb-9) clones were expanded and transiently transfected with a Cre expression cassette and placed under HAT selection. Control transfections without Cre did not yield any HAT-resistant clones. What follows is a more detailed description of the method employed in this example.

As depicted in FIG. 1A, the PGKHprt minigene was modified by the insertion of a loxP site from pBS64 (HindIII-EcoRI, Klenow blunt) into the unique XbaI site (Klenow blunt) in the hprt intron. Insertion of the loxP site did not disrupt the cassette's HAT resistance function (not shown). The loxP-Hprt cassette was divided into two overlapping pieces: $hprt_A3'$ , which contains the PGK promoter, the hprt exons 1 and 2, the loxP-intron, hprt exons 3–6, and the SV40 poly A signal. In FIG. 1A, $hprt_A5'$ and hprt3' have a 2 kb overlap including the loxP site; independently, $hprt_A5'$ and $hprt_A3'$ do not provide HAT resistance, but they do when co-electroporated. $Hprt_A5'$ and $hprt_A3'$ were ligated to positively selectable cassettes ($hprt_A3'$ to the pol II neo gene and $hprt_A5'$ to a PGK-puromycin resistance gene); in both cases, the positive markers replaced the deleted part of the loxP-Hprt cassette, ensuring that, upon recombination, they are separated from the reconstituted cassette. FIG. 1C depicts the general strategy for making deletions consisting of 3 steps: Step 1: conventional replacement-type gene targeting used to replace the Hoxb-1 gene with the $hprt_A3$ ' neo cassette; Step 2: ES cells identified as correctly targeted are used as a substrate to insert the $hprt_A5'$-puro cassette into the endogenous Hoxb-9 gene by conventional replacement-style targeting (the cis configuration is illustrated here); and Step 3: transient expression of Cre induces recombination between the loxP sites which reconstructs a functional hprt minigene. In FIG. 1 C4, the intra-chromosomal recombination pathway is illustrated, and in FIG. 1 C5, cells with the recombinant (deleted) chromosome to be positively selected in HAT media and a chromosomal ring are generated by the intra-chromosomal pathway. This is believed to be unstable and lost during the growth of the colony.

The targeting vector for Hoxb-1 consists of a 3.5 kb BglII-NcoI fragment (5' homologous arm); the Hoxb-1 coding sequence (1.7 kb Nco-BglII) was replaced by the $hprt_A3'$-neo cassette and a 2 kb BglII-PvuII fragment (3' homologous arm). The vector was linearized with SalI and a 10 μg was electroporated into hprt-negative AB2.2 ES cells. G418 selection was applied 24 hours after the electroporation and resistant clones were arrayed in 96 well plates, and targeted clones were detected by Southern analysis. A single targeted clone out of 384 clones analyzed was identified with the predicted structure of the targeted allele using probes 5' and 3' of the Hoxb-1 gene. This clone was expanded and transfected with the Hoxb-9 targeting vector. The targeting vector for Hoxb-9 consisted of a 6.2 kb HindIII fragment of homology which included exon 1. The $hprt_A5'$-puro cassette was cloned into the unique SalI site in exon 1. The orientation of the cassette was such that, when targeted, the loxP sites in the $hprt_A$cassettes would be in the same orientation. The vector was linearized and 10 μg of vector was electroporated into clone #298 AB2.2 cells and plated on SNLP (puro resistant SNL76/7 cells). Puromycin selection (5 μgml) was applied 24 hours after electroporation. Resistant clones were arrayed in 96 well plates and screened for targeted clones by Southern analysis. Double-targeted clones were detected at a frequency of 6%. Multiple independent double-targeted clones were expanded and independently transiently transfected (by electroporation) with 20 μg of a supercoiled Cre expression cassette pOG231. HAT selection was applied 48 hours after the electroporation. HAT-resistant clones were arrayed and analyzed by Southern Blot analysis.

As evidenced by Table 1, two classes of double-targeted clones could be distinguished by this assay.

TABLE 1

| | | Frequency ($10^{-7}$) | | |
| | | Deletion | | |
| Interval | Distance | I | II | Inversion |
|---|---|---|---|---|
| Hoxb9-Hoxb1 | 90 kb | 153 | 0.5 | ND |
| Hoxb9-E2DH | 3–4 cM | 6 | 1 | 43 |
| Gastrin-E2DH | 1 Mb | 470 | 1.8 | 334 |
| E2DH-Wnt3 | 3–4 cM | 30 | 4 | 19 |

Table 1 reports the frequency of Cre-mediated recombination as a function of distance between the loxP sites. Deletion frequencies are illustrated for both Class I and Class II clones while inversion frequencies are only illustrated for Class I clones.

One class (Type I) yielded HAT-resistant recombinants at frequencies averaging $1 \times 10^{-5}$ per treated cell, while a second class (Type II) yielded HAT-resistant clones at a much lower frequency.

Table 2 shows the frequency of Cre-mediated recombination as a function of distance between the loxP sites.

TABLE 2

Example B
RECOMBINATION FREQUENCY ON THE
MOUSE CHROMOSOME 11

| | Deletion | | Inversion | | Duplication | |
| Interval | Cis | Trans | Cis | Trans | Cis | Trans |
|---|---|---|---|---|---|---|
| Gastrin-E$_2$DH (1 Megabase) | 476 | 1 | 355 | 0 | 166 | 2 |
| E$_2$DH-D11MIT199 (2 cM) | 102 | 3 | 293 | 0 | N/A | N/A |
| HoxB-E$_2$DH (3–4 cM) | 2 | 0 | 43 | 0 | N/A | N/A |
| E$_2$DH-Wnt3 (3–4 cM) | 36 | 4 | 19 | 0 | N/A | N/A |
| E$_2$DH-D11MIT69 (22 cM) | 0 | 0 | 3 | 0 | N/A | N/A |

($1 \times 10^7$ ES cells were electroporated with 20 ug pOG 231 (Cre expression plasmid) and were selected with HAT medium.)

Table 2 is similar to Table 1, except that the former shows an additional deletion frequency for an additional interval (E$_2$DH-D11Mit69); it also shows duplication frequency; and finally it shows additionally deletion, inversion, and duplication frequencies for both cis- and trans-.

EXAMPLE C

Cis and Trans Recombination

Two types of clones might correspond to the cis or trans configuration of the loxP sites. The HAT-resistant clones derived at a high frequency from Type I clones might be products in intrachromosomal recombination or sister chromatid exchange (loxP sites in cis). Type II clones might require interchromosomal or inter-sister-chromatid recombination between homologous chromosomes (loxP sites in trans), which may occur relatively infrequently. These different pathways were distinguished by analyzing the markers in recombinant HAT-resistant clones.

Deletion of the HoxB cluster from a chromosome double targeted in cis would be accompanied by the loss of the neo and puro cassettes. These are either segregated (sister-chromatid pathway) or a ring is formed which is presumed to be unstable (FIG. 1). The loss of both markers could be documented in most of the HAT-resistant clones derived from Type I double-targeted clones, consistent with the hypothesized cis configuration of the Type I clones.

As anticipated, the consecutive targeting events and the Cre-induced recombination event results in the formation of novel restriction fragments (FIG. 2). External probes identify the novel junction fragments using an NheI digest since there is not an NheI site present in the loxP-hprt cassette. An internal probe confirms the loss of 90 kb of sequence by dosage difference between the wildtype and the deletion clones (FIGS. 2 E and F).

EXAMPLE D

E2DH-Gastrin 1 Mb Deletion

One of the goals behind the methods of the present invention is to construct chromosomal deletions so that regions of the genome can be tested for tumor suppressor activity. Many candidate regions have been identified from loss of heterozygosity (LOH) studies. One well-defined region in human breast cancer maps close to the Gastrin locus on human chromosome 17q close to BRCAL. Miki, et al., Science 266:66–71 (1994). This putative sporadic tumor suppressor locus maps in a conserved linkage group on mouse chromosome 11 between Gastrin and the E2DH locus. The generation of hemizygous mice with a deficiency that encompasses this locus functionally tests if this region contains a sporadic breast cancer gene that is involved in mammary neoplasia.

The large size of the regions which contain putative sporadic tumor suppressor loci complicates substantially the use of deletion strategy. In the absence of a YAC cloning contig which spans the relevant genetic interval, the gene order and orientations were not known. This is an important consideration since both the order and the orientation of the Hprt minigene fragments will determine the type of chromosomal rearrangement that is required to reconstruct a functional Hprt cassette. The possible orientations are illustrated in FIG. 1D. The recombinant chromosomes include deletions, duplications, inversions, and di- and acentric chromosomes (FIG. 1E). These rearranged chromosomes can be distinguished on Southern blots by the appearance of novel junction fragments, but the most rapid identification of the clones with deletions can be obtained from selection using neomycin and puromycin resistance cassettes which have been configured to lie between the loxP sites in the to-be-deleted interval (see FIG. 1).

To construct ES cell lines with large deletions between the Gastrin and the E2DH locus (containing SBC I) in the absence of a priori knowledge of the gene order and orientation, all four possible arrangements of the hprt minigene fragments were made and tested, only one of which will generate deletions. Two targeting vectors were constructed for each deletion endpoint representing the two possible orientations of the hprt minigenes. The $hprt_A3'$ cassette was targeted to the E2DH locus with the alternative minigene orientations (A or B). Targeted clones representing both the A and B orientations were, in turn, transfected with the targeting vectors representing the different orientations of the $hprt_A5'$ cassette (A or B) at the Gastrin locus. Multiple independent, targeted clones were isolated representing the four different minigene configurations to ensure that clones with the cis and the trans configurations were likely to be represented. Each of these clones was expanded, transfected with a Cre expression cassette and plated under HAT selection. What follows is a more detailed description of the method employed in this example.

Overlapping λ phage containing the mouse E2DH locus were isolated from a mouse 129Sv/Ev genomic library using a human E2DH cDNA probe. Unlike the duplicated human E2DH locus, the mouse locus is present at a single copy. λ phage containing the mouse Gastrin locus were isolated from the same library using a PCR fragment from the rat Gastrin cDNA. The mouse E2DH gene and Gastrin genes had not been mapped; to confirm that these genes mapped to mouse chromosome 11, a hamster/mouse hybrid cell line in which the mouse chromosome 11 is the only mouse genetic material was hybridized to probes specific for the mouse Gastrin and E2DH loci.

Standard gene replacement targeting vectors were constructed from these genomic clones. E2DH vector: a total of 8.0 kb of homology was used. The XhoI-XbaI 5.5 kb fragment containing the entire E2DH coding sequence was replaced with the $hprt_A3'$ minigene cassette in both orientations. In the Gastrin vector, a total of 7.5 kb of homology was used. The 3.5 kb XhoI-NheI fragment containing the Gastrin coding region was replaced with the $hprt_A5'$ cassette in both orientations.

The two vectors were separately transfected into AB2.2 ES cells. G418 resistant clones were obtained for each vector. Clones were gridded onto 96 well plates and screened for targeted clones. Targeted clones were identified at a ratio of 1/25 for the A orientation vector and 1/25 for the B orientation vector. The two types of targeted ES cells were assayed for totipotency by generating chimeras which tested for germ line transmission. Totipotent E2DH-targeted ES cell lines were identified for both the A and the B orientation and these were transfected with the vectors which target the Gastrin locus. Puromycin resistant clones were arrayed on 96 well plates and screened for targeted clones. All four classes of double targeted clones were obtained. For simplicity, this figure only shows the double targeted ES cell having the $hprt_A5'$ and $hprt_A3'$ cassettes in the A orientation and in cis.

The double targeted ES cell clones were transfected with the Cre expression plasmid as previously described. $HAT^r$ colonies were recovered and sibselected to test for puromycin and G418 resistance. Individual clones were expanded and analyzed for junction fragments using multiple probes. Each blot was hybridized with two probes, one from the E2DH locus and the other from the Gastrin locus. The frequency of obtaining HAT resistant colonies from the different clones is summarized in Table 3.

TABLE 3

| Category | Class | Clones tested | m HAT$^r$ (10$^7$) | G418 | Puro |
|---|---|---|---|---|---|
| AA | I | 4 | 470 | S | S |
|  | II | 2 | 1 | R | R/S |
| AB | I | 5 | 344 | R | R |
|  | II | 1 | 0 | — | — |
| BA | I | 3 | 377 | R | R |
|  | II | 2 | 0 | — | — |
| BB | I | 3 | 166 | R | R |
|  | II | 6 | 1.8 | R/S | R |

Table 3 reveals the frequency of the Cre-mediated recombination and retention of the markers in recombinant clones. All of the data is derived from the E2DH-Gastrin double targeted clones. The categories of clones are illustrated in FIG. 1D, and the expected products are described in FIG. 1E. Class I double-targeted clones give a high frequency of HAT-resistant recombinants, while Class II clones give a low frequency of HAT-resistant clones. Retrospective analysis has revealed that the class I clones and Class II clones have the targeted genes in cis and trans. S and R refer to resistance or sensitivity to G418 or puromycin as assayed by selection. Both resistant and sensitive clones were recovered.

Figure 3:
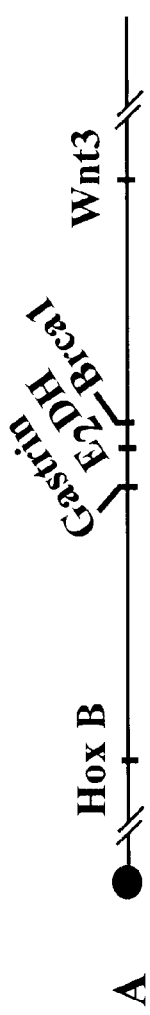
FIGS. 3A–3E: 3A: depicts mouse chromosome 11, and the loci used as endpoints for the chromosome engineering are illustrated. 3B: shows NheI restriction sites (N) and fragment lengths around the E2DH and Gastrin loci. 3C: shows chromosome 11 with both the E2DH and Gastrin loci targeted with the hprt$_A$5 and hprt$_A$3 vectors, respectively. For clarity, only the cis configuration and the A orientation are shown. 3D: shows the structure of the deletion, duplication and inversion alleles. The sizes of the diagnostic restriction fragments and probes used to detect these alleles are indicated. The deletion, duplication and inversion alleles are derived from the double targeted chromosome in the AA, BB and AB configurations, respectively. 3E: shows the results of Southern blots which confirm the structure of the recombinant chromosomes. The probes used with each blot (a, b, c or d) are indicated beneath each panel and on the diagrams of the various alleles. The lanes are coded as follows: wildtype (wt), double targeted (dt), deletion (del), duplication (dup) and inversion (inv).
Figure 3:
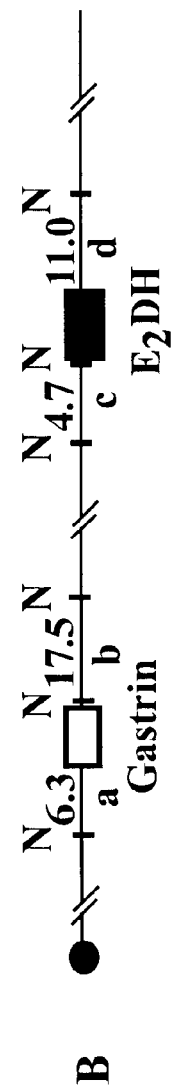
Figure 3E:
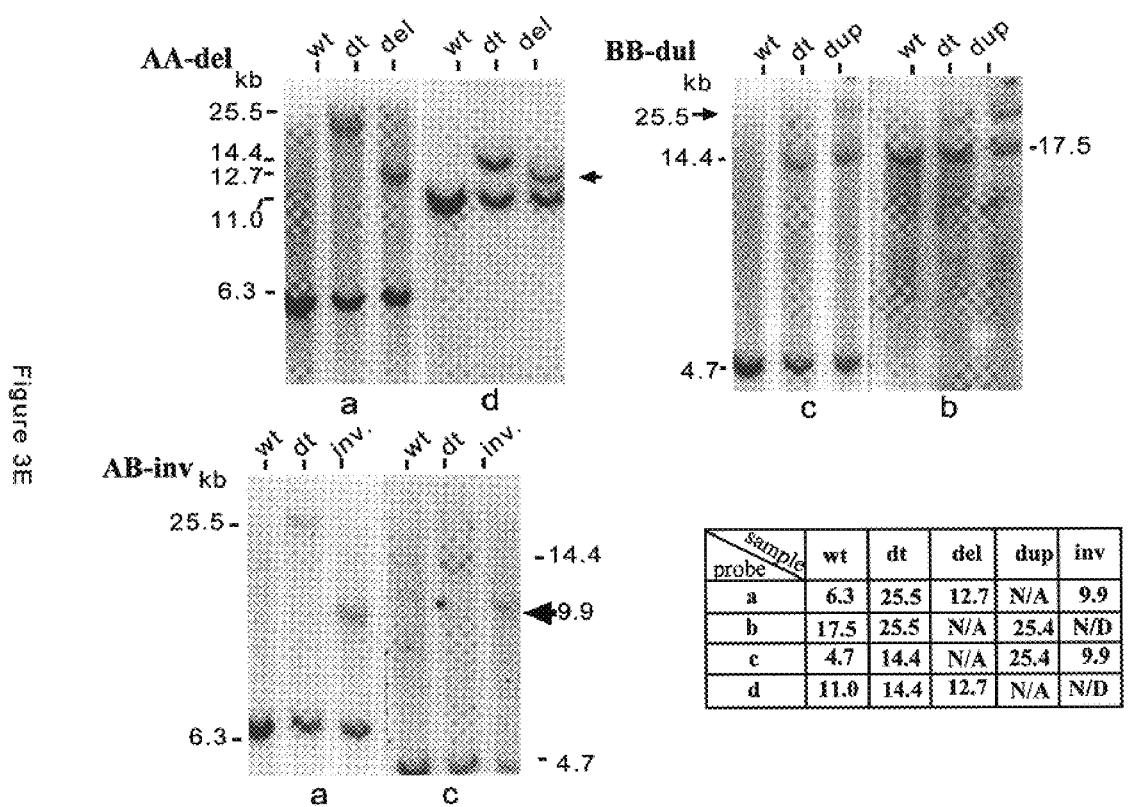

HAT-resistant clones were recovered from each of the four alternative split minigene configurations. The individual clones within a specific orientation group could be placed into one of two classes, based on the frequency with which HAT-resistant clones could be recovered (Table 3). Selection analysis identified the AA class I HAT-resistant clones as those that had lost the neomycin and puromycin resistance genes; these clones are the most likely to have the desired deletion. Since the AA class I clones gave the deletion product, this allows predictions to be made on the likely products of the alternative configurations: BB gives duplications, and AB or BA should give inversions. These predictions have been confirmed by detailed molecular analysis summarized in FIG. 3. In particular, the juxtaposition of the hprt minigene fragments which were previously positioned approximately 1 Mb apart in the genome results in unique junction fragments that are specific for the different types of rearrangement. The AA type II clones yield HAT-resistant recombinants at a low frequency. It was hypothesized that these clones represented the cases where the deletion selection cassettes had integrated in trans. Interchromosomal recombination would result in both the neo and puro resistance genes being located on one chromosome, while the reconstructed hprt minigene would be on the homologue. Thus it would be anticipated that all of the positive selection markers would be retained in such a cell. Sibselection identified two classes of HAT-resistant clones which were represented at approximately equal frequencies. One type only retained the neo cassette, and a second type retained both the neo and the puromycin resistance cassettes (Table 1A). The segregation of the puro resistance gene from the neo cassette is explained readily if Cre-induced recombination between sister chromatids (FIG. 4) occurred. This occurrence was confirmed by the molecular analysis of these clones. While the clones with the duplicated and deleted chromosomes can be generated by either interchromosomal or non-sister chromatid exchange, the clones which only carry the neo cassette can only have arisen by the non-sister chromatid recombination pathway. These clones have been confirmed to carry both the deletion chromosome and the non-recombinant chromosome with only the E2DH targeted locus (FIG. 4).

Figure 5:
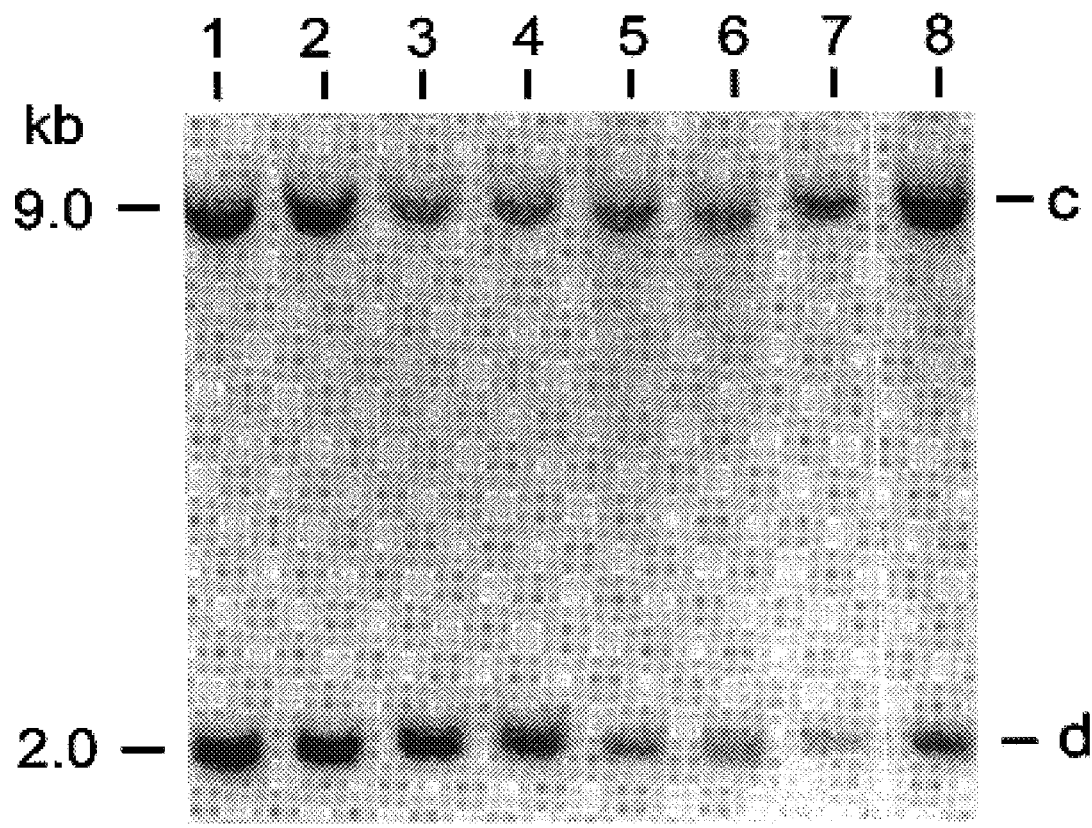
FIG. 5 Gene dosage analysis and segregation of the deletion and duplication chromosomes through the mouse germ line are demonstrated: Lane 1: wild type allele (AB2.2 ES cell line); Lane 2: ES cell clone with the duplication and deletion (genetically balanced); Lanes 3 to 6: transmission and segregation of the duplication and deletion alleles in the progeny of a chimeric male constructed from the cells shown in lane 2. Lanes 3 and 4 show mice with the deletion, lanes 5 and 6 show mice with the duplication; the increase or decrease in intensity of the 9.0 kb fragment relative to the 2.0 kb control fragment is consistent with junction fragment analysis of the inheritance of the duplication or deletion alleles from these mice (data not shown). Lanes 7 and 8 show mice from heterozygous mating homozygous for the duplication allele which is evident from the increased intensity of the 9.0 kb fragment.

The clones with the deletion on one chromosome and the duplication on the other are genetically balanced. Therefor these clones were considered to be the best candidates for germ line transmission. Four independent clones were injected into blastocysts, representing clones descended from both the A and B orientation of the E2DH targeted allele. Alleles from three of these clones were transmitted into the germ line, despite three cycles of subcloning and expansion. Segregation of the deletion and duplication alleles from a chimeric male is illustrated by gene dosage analysis (FIG. 5). Mice which are hemizygous for this deletion (1 copy) are fully viable. Mice which are heterozygous for the duplication (3 copies) or homozygous (4 copies) are also fully viable (FIG. 5) and fertile.

EXAMPLE E

Deletion of Two 3–4 Centimorgan Regions on Chromosome 11

Figure 6A:
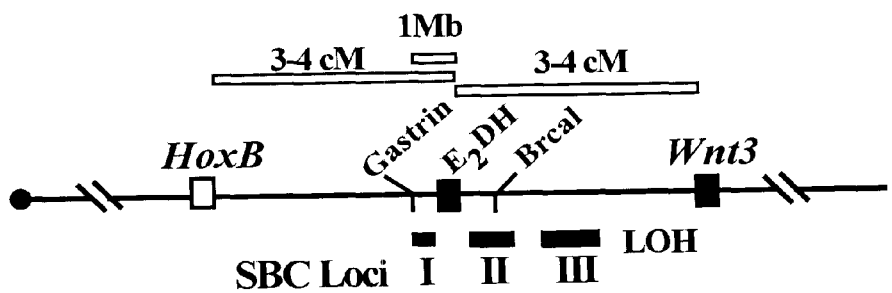
FIGS. 6A–6C: Deletion of two 3–4 cM intervals on mouse chromosome 11 is shown. 6A depicts mouse chromosome 11. The shaded bars indicate the intervals which are to be deleted. Hox B, E2DH and Wnt3 are the loci which serve as the deletion endpoints. SBC (Sporadic Breast Cancer) loci are indicated by the black bars. These loci are the putative location of tumor suppressor genes based on the analysis of loss of heterozygosity in breast cancer. 6B depicts a double-targeted chromosome which has been targeted with the $hprt_A3'$ cassettes to the Hoxb9 and E2DH genes or to the E2DH and Wnt3 genes. The A orientation E2DH-targeted clones were used with the HoxB-E2DH deletion and the B orientation clones were used with the E2DH-Wnt3 deletion. Only the orientations of the $hprt_A5'$ cassette which give the deletion products are illustrated. The vertical bars represent NheI sites; the sizes of the fragments are indicated and the probes are indicated by shaded boxes labelled c and d. 6C shows the structure of deletion alleles. Diagnostic NheI fragments for the deletion are indicated. 6D reveals the Southern analysis that confirms the structure of the alleles in the wildtype (wt), double-targeted (dt) and deletion (dt) clones. The deletion-specific junction fragments are indicated by the arrows.
Figure 6B:
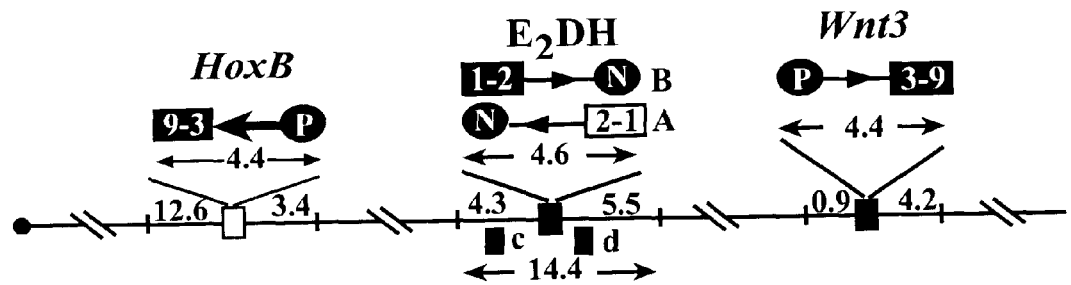
Figure 6C:
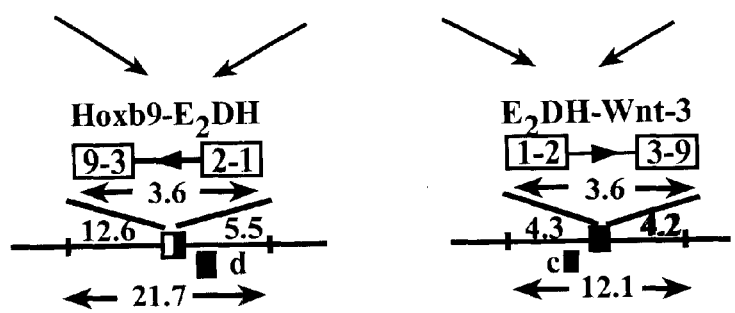

Given the apparent insensitivity of the Cre-induced recombination to the distance between the loxP-hprt substrates, two additional experiments were performed to investigate if Cre could delete a larger fragment. Two 3–4 cM intervals were chosen, proximal or distal to the E2DH locus on mouse chromosome 11. This region is syntectic with a region on human chromosome 17q where loss of heterozygosity studies have identified several distinct regions that are likely to contain tumor suppressor genes which are mutated in 30–70% of sporadic breast cancer. These regions have been termed SBCI, SBCII and SBCII (FIG. 6A).

Figure 6D:
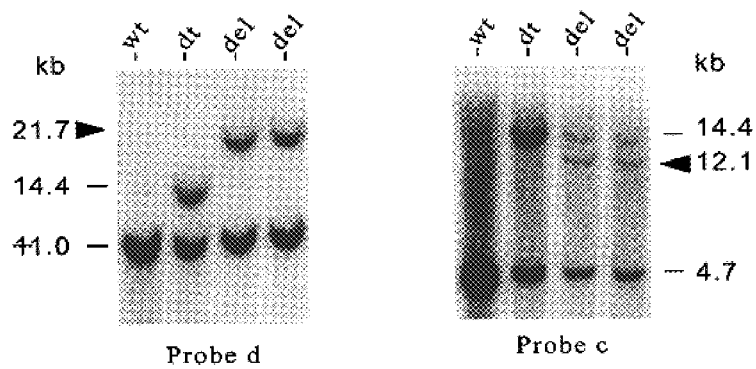

Since the E2DH-Gastrin deletion had revealed the orientation of the E2DH locus, one of the A orientation E2DH-targeted clones was selected for the proximal deletion and a B orientation E2DH-targeted clone was selected for the distal deletion. Targeting vectors (two orientations) were constructed for the HoxB locus (Hoxb-9) and for Wnt3 (see Roelink, et al., *PNAS USA* 87:4519–23 (1990)). Double-targeted clones were generated, transfected with the Cre expression cassette and HAT-resistant clones were selected. One vector orientation yielded G418 and puro sensitive clones which were hypothesized to have a 3–4 cM deletion, while the other orientation yielded HAT-resistant clones which all retain the neo and puro cassettes. This latter category of clones were confirmed to be inversions of the 3–4 cM interval by molecular analysis. The molecular analysis of the G418 and puro sensitive clones identified two classes of clones that occur with approximately equal frequency. The first type of clone was consistent with a simple deletion event, illustrated for the Hoxb9-E2DH deletion (FIG. 6D). The other class of clone exhibited the expected deletion junction fragment, but also retained a junction fragment that is diagnostic for the targeted chromosome, but should have been lost during the deletion event (illustrated for the E2DH-Wnt3 deletion in FIG. 6D). The retention of this junction fragment and the acquisition of the expected deletion-specific fragment in about half the clones can be explained by two different recombination pathways. The pure clones are believed to be products of an inter-chromosomal pathway (FIG. 1C), while those clones that retain the primary targeted allele may reflect a sister-chromatid exchange. While the duplicated chromosome should be segregated to a daughter cell and does not carry the reconstructed hprt minigene, extensive metabolic co-operation between the hprt$^+$ and hprt$^{31}$ ES cells in a colony facilitate cross rescue and substantial contribution of the hprt$^-$ daughter cells to the HAT-resistant clones. What follows is a more detailed description of the method employed in this example.

E2DH and Hoxb9 vectors have been described previously. Wnt3 genomic clones were isolated from a 129Sv/Ev genomic library using a cDNA probe. Conventional replacement targeting vectors containing 7.0 kb of homology were constructed. The hprt$_A$5' cassette replaces a 2.1 fragment (contains exons 3 and 4) of the Wnt3 gene. The Hoxb9 vectors and the Wnt3 vectors were independently targeted into the E2DH targeted cell lines. An "A" orientation clone was used for the Hoxb9 targeting vectors. Transfected cells were selected in puromycin and targeted clones were identified as previously described. Multiple independent double targeted clones were transfected with the Cre recombinase. HAT-selection was used to isolate recombinant clones which were sib-selected and tested by Southern analysis for the predicted junction fragments.

EXAMPLE F

Using a Virus Rather Than Targeting to Efect the Recombination

Figure 7:
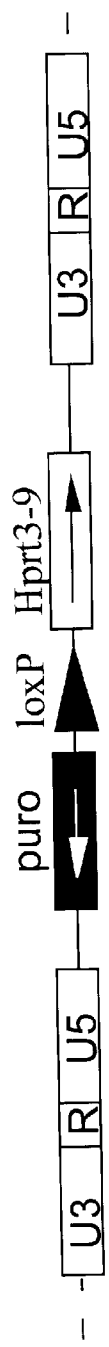
FIG. 7: Schematic representation of a provirus structure, containing $hprt_A5'$ minigene cassette, a loxP site, and a puromycin resistance gene, for use as a vector in one embodiment of the present invention. This particular vector would insert the loxP site at the 5' end of the chromosome.

Rather than relying on traditional targeting techniques, either or both of the desired deletion endpoints can be added to the genome by means of a retrovirus. In this example, a viral vector is used to insert the endpoint at the 5' end only. FIG. 7 is a schematic representation of a provirus structure suitable for this use, which is comprised of an hprt$_A$5' minicassette, a loxP site and a puromycin resistance gene. Hence, the provirus structure is similar to the non-viral targeting vectors described in the previous examples.

In this example, only the 5' endpoint was inserted using the viral vector depicted in FIG. 7, though in other embodiments, both endpoints can be added using viral vectors. Chromosomal deletions were induced using the methods substantially as described in the previous examples. Hence, insertions are made at the two endpoints framing the desired chromosomal deletion. The insertions are preferably made one at a time, and involve replacing a first native sequence (i.e., the first endpoint) on the chromosome of interest with a first selection cassette. This selection cassette consists of three elements: a first selectable marker, a loxP site located in the hprt minigene intron, and a first portion of a second selectable marker, preferably a non-functional fragment of an Hprt minigene cassette. The first selectable marker is preferably a neomycin resistance gene (hprt$_A$5' cassette) or a puromycin resistance cassette (hprt$_A$3' cassette). The cells expressing the marker (either the neomycin resistance gene or the puromycin resistance gene) are then selected. Next, the process is essentially repeated for second endpoint on the chromosome of interest. Thus, the cells selected possess both loxP sites framing the desired portion of the chromosome to be deleted. The difference in this step is that the hprt minigene fragment—also non-functional—is the complementary portion to that inserted into the first endpoint. Third, the selected cells are contacted with Cre, which may be expressed in one of the three ways described above, which induces recombination between the loxP sites. This recombination generates a fully functional Hprt minigene. This minigene provides resistance to HAT selection in hprt deficient cells. Additionally, the positive selectable markers are positioned so that following recombination, they are lost from the deleted chromosome. Therefore, the methods for inducing the deletion described in this example are nearly identical to those for practicing the method using a non-viral vector. Inherent differences in method and technique that result from using a viral versus non-viral vector are well-known to the skilled artisan, hence a detailed description of any embodiment of the method of the present invention involving non-viral vectors could be easily adapted by the skilled artisan using a viral vector. The recombination efficiencies obtained from using the viral vector (described in FIG. 7) at the 5' endpoint are shown below in Table 4.

TABLE 4

| | # cell out of $10^7$ cre electroporated ES cells | | | |
|---|---|---|---|---|
| | HAT$^r$ | Puro$^r$ | NO Drug | Rec Efficiency |
| plate #3 | 275 | $1.62 \times 10^5$ | $3.9 \times 10^5$ | $1.7 \times 10^{-3}$ |
| plate #4 | 388 | $2.54 \times 10^5$ | $3.9 \times 10^5$ | $1.5 \times 10^{-3}$ |
| Average | 331 | $2.09 \times 10^5$ | $3.9 \times 10^5$ | $1.6 \times 10^{-3}$ |

EXAMPLE G

Figure 8:
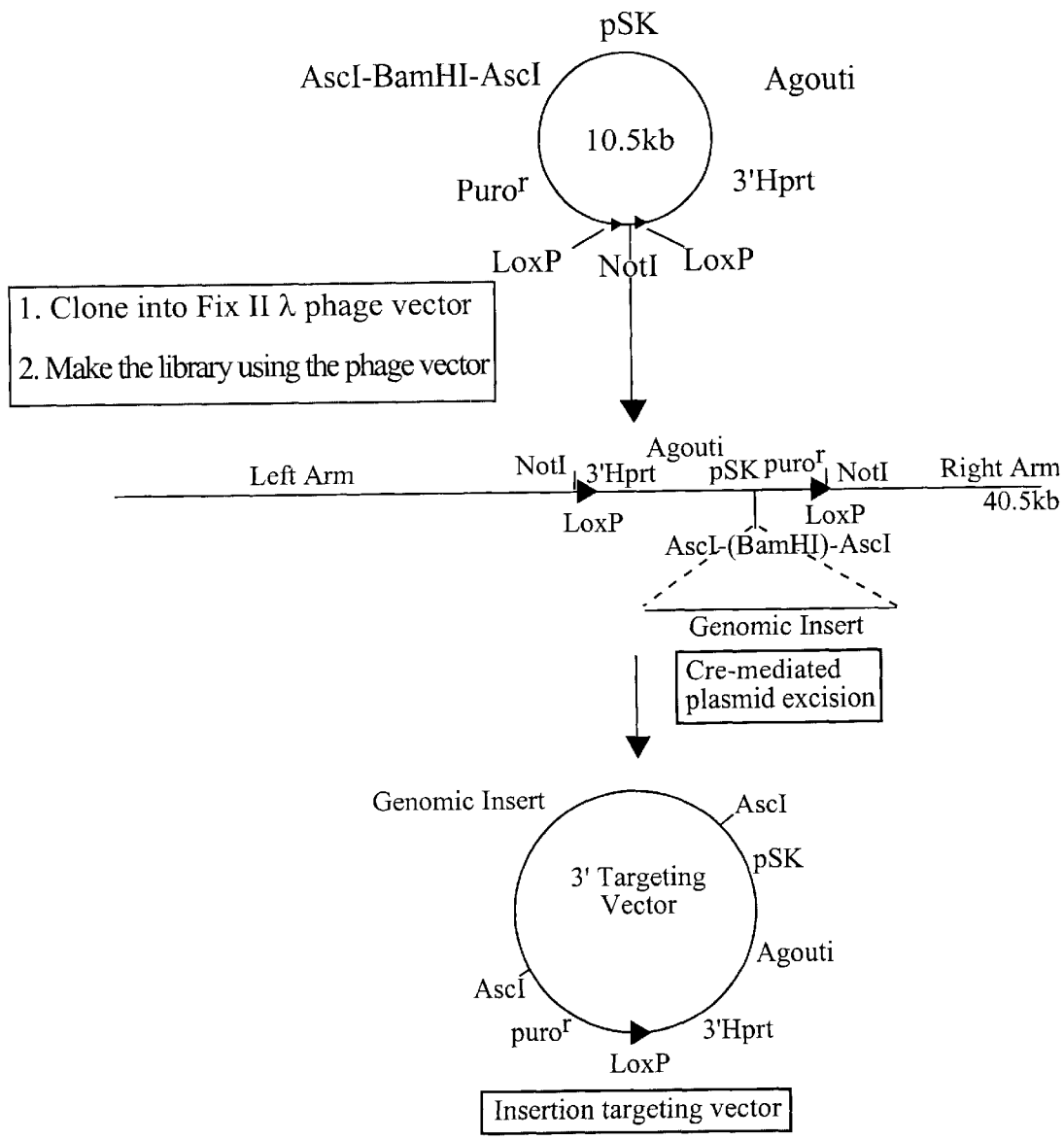
FIG. 8: A 3' anchor library that contains the expression cassette 3' hprt, puromycin resistance gene, and k14-agouti gene.
Figure 9:
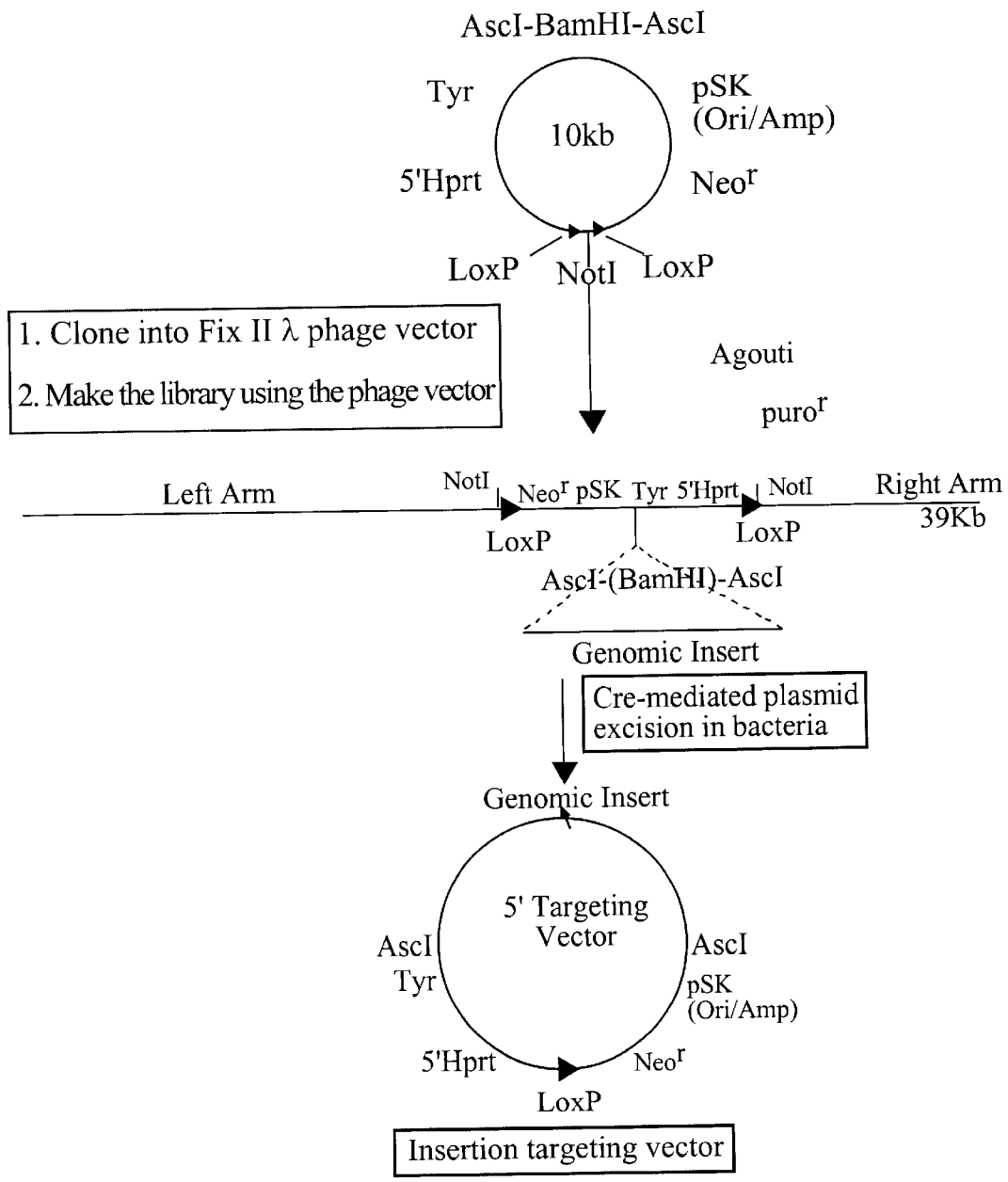
FIG. 9: A 5' anchor library that contains the expression cassettes 5' hprt, neomycin resistance gene, and tyrosinase gene.
Figure 10:
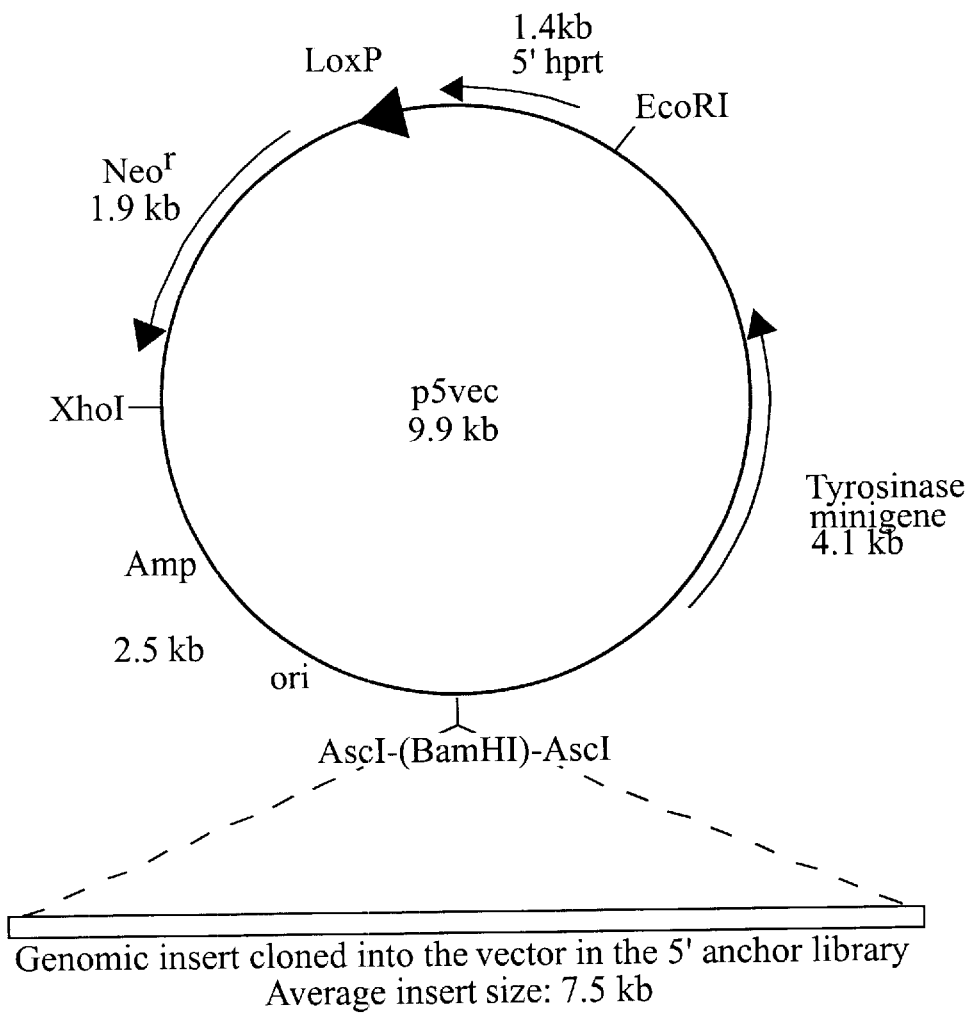
FIG. 10: Map of an exemplary 5' endpoint targeting vector automatically excised out of a phage clone isolated from the 5' anchor library.
Figure 11:
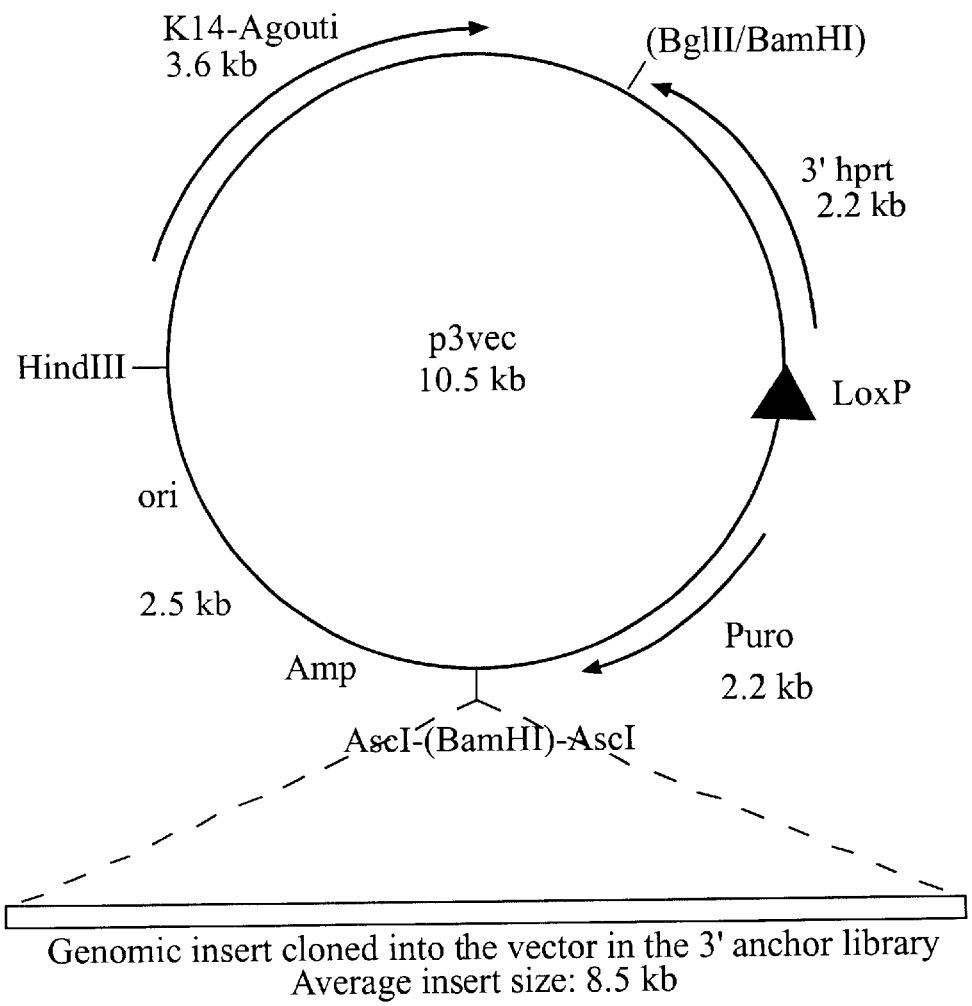
FIG. 11: Map of an exemplary 3' endpoint targeting vector automatically excised out of a phage clone isolated from the 3' anchor library.
Figure 12:
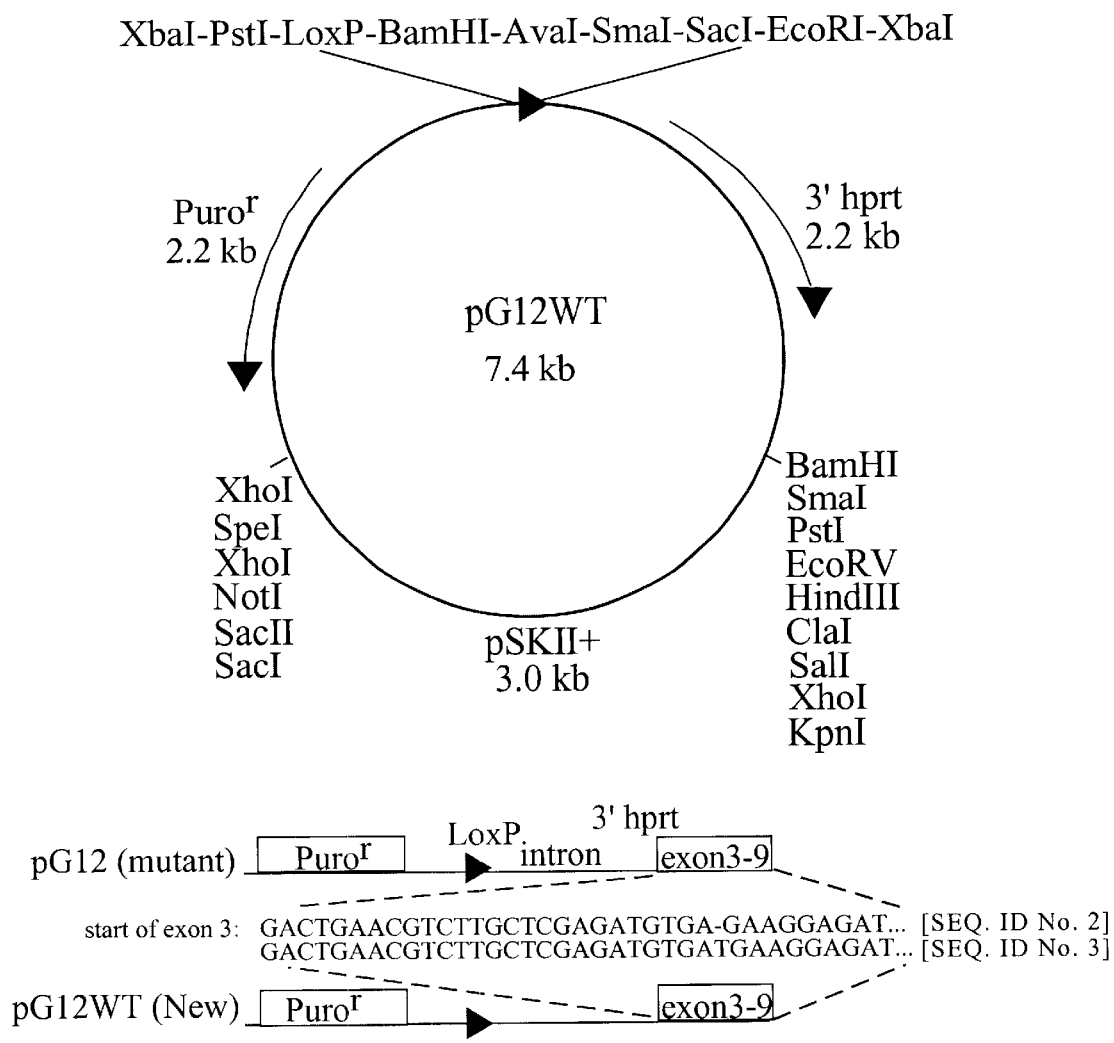
FIG. 12: Map of pG12WT (Wildtype 3' hprt cassette plasmid for making chromosomal rearrangements). The sequence is identical to pG12 except that the mutation in 3' hprt has been fixed.

Frequency of Cre-induced Deletion Between E$_2$DH and D11 Mit199 Using An Improved Targeting Vector This example illustrates the enhanced Cre-induced deletion frequency using a different targeting vector compared with that used in the previous examples. The details of the protocol are substantially as described in the previous examples. Details of this "improved vector" compared with the vector used in the previous examples are shown in FIGS. 10 through 12 (the original vector is shown by comparison in FIG. 12). FIG. 10 shows a map of an exemplary 5' endpoint targeting vector automatically excised out of a phage clone isolated from the 5' anchor library. The 5' anchor library is shown in FIG. 9; this anchor library contains the expression cassettes 5' hprt, neomycin resistance gene, and tyrosinase gene. FIG. 11 shows a map of an exemplary 3' endpoint targeting vector automatically excised out of a phage clone isolated from the 3' anchor library. The 3' anchor library is shown in FIG. 8; this anchor library contains the expression 20 cassette 3' hprt, puromycin resistance gene, and k14agouti gene. FIG. 12 shows a map of pG12WT (Wildtype 3' hprt cassette plasmid for making chromosomal rearrangements). At the bottom of FIG. 12, a comparison of the sequence used to generate the data in Examples B–E versus the sequence used to generate the data in this and following examples is shown. As evidenced by FIG. 12, the two sequences are identical to pG12 except that the mutation in 3' hprt of the wildtype cassette plasmid has been fixed.

Figure 13:
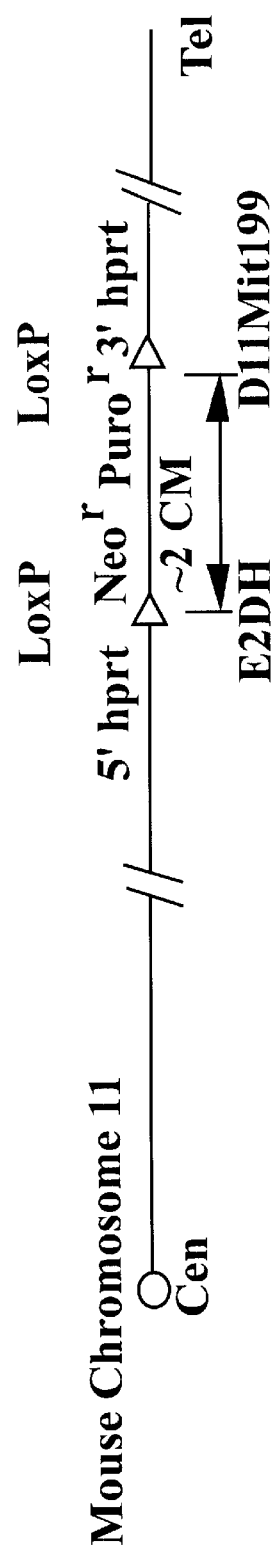
FIG. 13: Map of a portion of the mouse chromosome 11 showing the general composition of the selection cassettes positioned at the chromosome endpoints, and the position of the Ore-induced deletion interval, $E_2DH-D11Mit199$.

FIG. 13 shows the portion of the mouse chromosome 11 at which the deletion strategy is directed; FIG. 13 also shows the general composition of the selection cassettes positioned at the chromosome endpoints, and the position of the Cre-induced deletion interval, E$_2$DH-D11Mit199.

Table 4 shows the frequency of Cre-induced deletion between E$_2$DH and D11Mit199, which can be compared with Tables 1B, 1B, and 4. The frequency shown is the number of HAT-resistant colonies per Cre-electroporated cell. The numbers are obtained by averaging data from at least two experiments with at least two cell lines (except for the new vector in the trans configuration). A comparison of the data presented in Table 4 with those in Tables 1, 2, and 3 reveal that the cassette shown in FIG. 11 mediates recombination approximately $10^3$ more efficiently than the cassette used to generate the data in Tables 1, 2, and 4.

EXAMPLE H

Frequency of Cre-induced Deletion Between E$_2$DH and D11 Mit69 Using An Improved Targeting Vector Similar to Example H, this example also illustrates the enhanced Cre-induced deletion frequency using a different targeting vector compared with that used in the previous examples. Example H illustrates the Cre-induced deletion frequency between E₂DH and D11Mit199-a distance of about 2 CM. By contrast, Example I illustrates the Cre-induced deletion frequency between E₂DH and D11Mit69-a distance of about 22 CM). The details of the protocol are substantially as described in the previous examples. Details of this "improved vector" compared with the vector used in the previous examples are shown in FIGS. 10 through 12 (the original vector is shown by comparison in FIG. 12). FIG. 10 shows a map of an exemplary 5' endpoint targeting vector automatically excised out of a phage clone isolated from the 5' anchor library. The 5' anchor library is shown in FIG. 9; this anchor library contains the expression cassettes 5' hprt, neomycin resistance gene, and tyrosinase gene. FIG. 11 shows a map of pG12WT (Wildtype 3' hprt cassette plasmid for making chromosomal rearrangements). The sequence is identical to pG12 except that the mutation in 3' hprt has been fixed.

Figure 14:
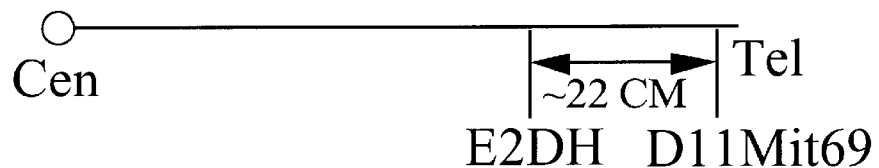
FIG. 14: Map of a portion of the mouse chromosome 11 showing the general composition of the selection cassettes positioned at the chromosome endpoints, and the position of the Cre-induced deletion interval, $E_2DH-D11Mit69$.
Figure 14:
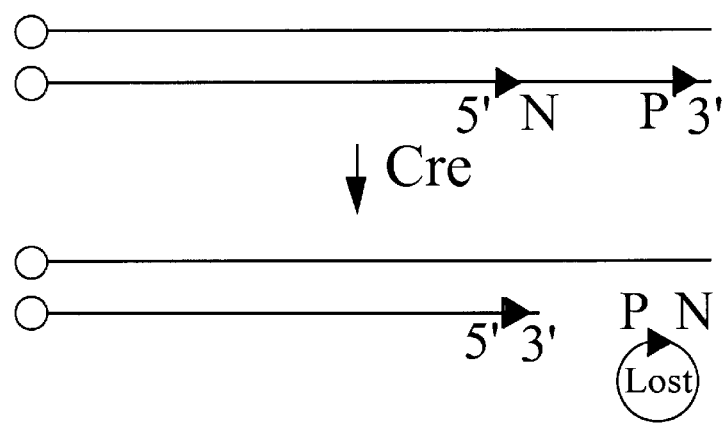
Figure 14:
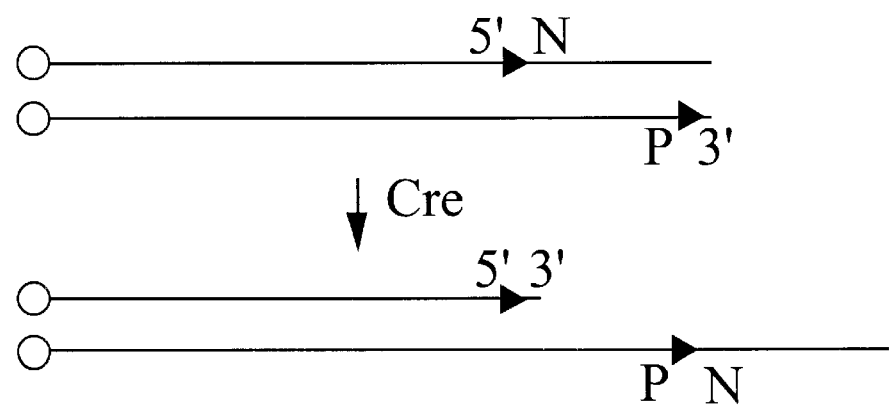

FIG. 14 shows the portion of the mouse chromosome 11 at which the deletion strategy is directed; FIG. 14 also shows the general composition of the selection cassettes positioned at the chromosome endpoints, and the position of the Cre-induced deletion interval, E₂DH-D11Mit69. Table 6 shows the frequency of Cre-induced deletion between E₂DH and D11Mit69, which can be compared with Tables 1A, 1B, and 4.

TABLE 6

Example H

| Markers | Frequency |
|---|---|
| HAT$^r$, Puro$^s$, Neo$^2$ | $5.8 \pm 3.3 \times 10^{-6}$ (n = 5)/$2 \times 10^{-5}$ (n = 1) |
| HAT$^r$, Puro$^r$, Neo$^r$ | $1.1 \pm 0.4 \times 10^{-5}$ (n = 10)/$3 \times 10^{-5}$ (n + 1) |

Two frequencies are reported in each row, reflecting two separate trials. The "frequency" of Cre-induced loxP recombination is expressed as the number of HAT$^r$ colonies per Cre-electroporated cell. The number of independent doubly targeted cell lines is denoted by "n=."

TABLE 5

Example G

| 3' hprt cassette | Cis | Trans |
|---|---|---|
| Old (mutant) | $2 \pm 0.5 \times 10^{-5}$ | $6.5 \pm 3.2 \times 10^{-7}$ |
| New (wildtype) | $2.3 \pm 1.3 \times 10^{-2}$ | $1.5 \times 10^{-4}$ |

What is claimed is:

1. A method for deleting, duplicating or inverting a selected region of genetic material in cells comprising the steps of:
   inserting a first selection cassette at a 5' end of said selected region using gene targeting methods, said first selection cassette comprising a first selectable marker, a first lox recombination site, and a first portion of a second selectable marker;
   selecting cells expressing said first selectable marker;
   inserting a second selection cassette at a 3' end of said selected region using gene targeting methods, said second selection cassette comprising a third selectable marker, a second lox recombination site, and a remaining portion of said second selectable marker;
   selecting cells expressing said third selectable marker;
   expressing a recombinase to produce recombination between said first and second lox sites; and
   selecting cells expressing said second selectable marker.

2. A method of claim 1 wherein said lox sites are loxP.

3. A method of claim 1 wherein said recombinase is Cre recombinase.

4. A method for inverting a selected region of genetic material in cells comprising the steps of:
   inserting a first selection cassette at a 5' end of said selected region using gene targeting methods, said first selection cassette comprising a first selectable marker, a first loxP recombination site, and a first portion of a second selectable marker;
   selecting cells expressing said first selectable marker;
   inserting a second selection cassette at a 3' end of said selected region using gene targeting methods, said second selection cassette comprising a third selectable marker, a second loxP recombination site, and a remaining portion of said second selectable marker;
   selecting cells expressing said third selectable marker;
   expressing Cre recombinase to produce recombination between said first and second loxP sites; and
   selecting cells expressing said second selectable marker.

5. The method of claim 4 wherein said first selectable marker is a puromycin resistance gene, said second selectable marker is an Hprt gene, and said third selectable marker is a neomycin resistance gene.

6. The method of claim 4 wherein said first selectable marker is a puromycin resistance gene.

7. The method of claim 4 wherein said second selectable marker is a functional Hprt gene.

8. The method of claim 4 wherein said third selectable marker is a neomycin resistance gene.

9. The method of claim 4 wherein said cells are embryonic stem cells.

10. The method of claim 4 wherein said Cre is transiently expressed Cre.

11. The method of claim 4 wherein said Cre is inducibly expressed Cre.

12. The method of claim 4 wherein said Cre is constitutively expressed Cre.

13. A method of inverting a selected region of genetic material in cells comprising the steps of:
   inserting a gene selection cassette at a 5' end of said selected region using either a gene targeting vector or a first viral vector, said first selection cassette comprising a first selectable marker, a first loxP recombination site, and a first portion of a second selectable marker;
   selecting cells expressing said first selectable marker;
   inserting a second selection cassette at a 3' end of said selected region using a second gene targeting vector or a second viral vector, said second selection cassette comprising a third selectable marker, a second loxP recombination site, and a remaining portion of said second selectable marker;
   selecting cells expressing said third selectable marker;
   expressing transiently Cre recombinase to produce recombination between said first and second loxP sites; and
   selecting cells expressing said second selectable marker.

14. The method of claim 13 wherein at least one viral vector is a retrovirus.

15. The method of claim 13 wherein at least one viral vector has a provirus structure comprising a cassette in turn comprising an hprt5' cassette, a loxP site, and a puromycin resistance gene.

16. The method of claim 13 wherein at least one viral vector has a provirus structure comprising a cassette in turn comprising an hprt5' cassette, a loxP site, and a neomycin resistance gene.

17. The method of claim 13 wherein the first targeting vector is a first vector for inserting a first native sequence of DNA at said 5' end, comprising:
   said first native sequence of DNA cloned into the vector of about 7.5 kb;
   a tyrosinase mingene;
   a neomycin resistance gene;
   a 5' hprt fragment; and
   a loxP site in a hprt fragment intron; and
   said second targeting vector for inserting a second native sequence of DNA at said 3' end, comprising:
      said second native sequence of DNA cloned into the vector of about 7.5 kb;
      a K14-agouti gene;
      a puromycin resistance gene;
      a 3' hprt fragment; and
      a loxP site in a hprt fragment intron.

18. The method of claim 13 wherein the first viral vector is a first vector for inserting a first native sequence of DNA at said 5' end, comprising:
   sad first native sequence of DNA cloned into the vector of about 7.5 kb;
   a tyrosinase mingene;
   a neomycin resistance gene;
   a 5' hprt fragment; and
   a loxP site in a hprt fragment intron; and
   said second viral vector for inserting a second native sequence of DNA at said 3' end, comprising:
      said second native sequence of DNA cloned into the vector of about 7.5 kb;
      a K14-agouti gene;
      a puromycin resistance gene;
      a 3' hprt fragment; and
      a loxP site in a hprt fragment intron.

19. A method for creating a defined chromosomal inversion comprising the steps of:
   identifying a desired region of a chromosome of interest to be inverted;
   inserting two sequences which are native to the chromosome of interest at each endpoint of said region of said chromosome of interest using a first and a second targeting vector, wherein each targeting vector is comprised of one or more selectable markers and a loxP site and an hprt fragment;
   transiently expressing Cre recombinase to produce recombination between each of two said loxP sites;
   whereby upon chromosomal rearrangement induced by said Cre recombinase, a functional hprt expression cassette is reconstructed, wherein the defined chromosomal inversion is created.

* * * * *